US011690547B2

(12) United States Patent
Nakae et al.

(10) Patent No.: US 11,690,547 B2
(45) Date of Patent: Jul. 4, 2023

(54) DISCERNMENT OF COMFORT/DISCOMFORT

(71) Applicants: Osaka University, Osaka (JP); PaMeLa, Inc.

(72) Inventors: Aya Nakae, Osaka (JP); Takahiro Soshi, Osaka (JP)

(73) Assignees: OSAKA UNIVERSITY, Osaka (JP); PAMELA, INC., Osaka (JP)

(*) Notice: Subject to any disclaimer, the term of this patent is extended or adjusted under 35 U.S.C. 154(b) by 635 days.

(21) Appl. No.: 16/634,310

(22) PCT Filed: Jul. 27, 2018

(86) PCT No.: PCT/JP2018/028300
§ 371 (c)(1),
(2) Date: Jan. 27, 2020

(87) PCT Pub. No.: WO2019/022242
PCT Pub. Date: Jan. 31, 2019

(65) Prior Publication Data
US 2020/0178888 A1    Jun. 11, 2020

(30) Foreign Application Priority Data
Jul. 28, 2017  (JP) .................................. 2017-146553

(51) Int. Cl.
*A61B 5/16* (2006.01)
*G06N 20/10* (2019.01)
(Continued)

(52) U.S. Cl.
CPC .............. *A61B 5/165* (2013.01); *A61B 5/316* (2021.01); *A61B 5/377* (2021.01); *A61B 5/4824* (2013.01);
(Continued)

(58) Field of Classification Search
CPC ....... A61B 5/4824; A61B 5/165; A61B 5/377; G06K 9/623; G16H 20/70
See application file for complete search history.

(56) References Cited

U.S. PATENT DOCUMENTS 9,241,665 B2    1/2016  Decharms
2005/0144042 A1*  6/2005  Joffe ...................... G16H 10/60
705/2

(Continued)

FOREIGN PATENT DOCUMENTS

JP    2013-255742 A1    12/2013
WO   2011/155196 A1    12/2011
(Continued)

OTHER PUBLICATIONS

Supplementary European Search Report and European Search Opinion, issued in connection with corresponding European counterpart 18838241.0 dated Jul. 8, 2021.
(Continued)

*Primary Examiner* — Vernal U Brown
(74) *Attorney, Agent, or Firm* — Muncy, Geissler, Olds & Lowe, P.C.

(57) ABSTRACT

The computer implemented method makes it possible to discern, for a variety of sensations, whether a sensation is a pleasant (comfortable) sensation or a sensation of discomfort. A classifier is generated for discerning the stress or comfort/discomfort of a subject. The method comprising: a) imparting, to a subject, different stimuli under the same environment, and obtaining brain wave data or analysis data thereof for the environment; b) correlating a reaction of the subject relating to the stimulation and the difference of the brain wave data or analysis data thereof obtained under the environment; c) generating a classifier for discerning the stress or comfort/discomfort of the subject, on the basis of
(Continued)

Pain context effect of same high temperature stimulation (subjective evaluation)

the correlation; and d) performing comfort/discomfort discernment using a basic step for amplifying a sample from a small stimulation.

10 Claims, 28 Drawing Sheets

(51) Int. Cl.
    *A61B 5/00*      (2006.01)
    *G06F 3/01*      (2006.01)
    *A61B 5/316*     (2021.01)
    *A61B 5/377*     (2021.01)

(52) U.S. Cl.
    CPC ............ *G06F 3/015* (2013.01); *G06N 20/10* (2019.01); *G06F 2218/14* (2023.01)

(56) References Cited

U.S. PATENT DOCUMENTS

| | | | | |
|---|---|---|---|---|
| 2008/0304667 | A1* | 12/2008 | Mihaljevic | G06F 7/582 380/268 |
| 2012/0288108 | A1 | 11/2012 | Adachi et al. | |
| 2013/0039498 | A1 | 2/2013 | Adachi et al. | |
| 2015/0134578 | A1 | 5/2015 | Tamatsu et al. | |
| 2015/0297109 | A1* | 10/2015 | Garten | A61B 5/316 600/28 |
| 2017/0042439 | A1* | 2/2017 | Yeow | G16H 10/60 |
| 2018/0184935 | A1* | 7/2018 | Han | H04W 4/38 |
| 2018/0190376 | A1* | 7/2018 | Hill | G06T 19/006 |
| 2018/0242904 | A1 | 8/2018 | Nakae | |
| 2019/0223783 | A1 | 7/2019 | Nakae | |

FOREIGN PATENT DOCUMENTS

| | | |
|---|---|---|
| WO | 2012/070212 A1 | 5/2012 |
| WO | 2013140106 A1 | 9/2013 |
| WO | 2014/151874 A1 | 9/2014 |
| WO | 2016125158 A1 | 8/2016 |
| WO | 2016/136361 A1 | 9/2016 |
| WO | 2018/038121 A1 | 3/2018 |

OTHER PUBLICATIONS

PCT Search Report and Written Opinion issued in connection with corresponding PCT Application No. PCT/JP2018/028300 dated Oct. 23, 2018.

Aoki, Hideki, et al., "On the Fluctuations in Electroencephalogram during Pain Sensation", Graduate School of Information Sciences, Tohoku University, *Miyagi University of Education. Institute of Electronics, Information, and Communication Engineers, pp. 71-78.

Voneda Tohru, et al., "Measurement of Event-related Potentials to Novel Electrical Stimuli with Painful Sensation", The Institute of Electronics, Information, and Communication Engineers. Graduate School of Information Sciences, Tohoku University, *Miyagi University of Education, p. 7-12.

* cited by examiner

FIG.4

Differentiation of stimulation type with different degree of unpleasantness:
Feature ranking and differentiation accuracy

| Features | | Ranking | Differentiation accuracy (%) |
|---|---|---|---|
| Cz | Amplitude | 1 | 40.244 |
| C3 | α | 2 | 50.000 |
| Cz | β | 3 | 36.585 |
| Fz | δ | 4 | 51.220 |
| Cz | γ | 5 | 56.098 |
| C4 | β | 6 | 47.561 |
| C3 | δ | 7 | 41.463 |
| Cz | α | 8 | 42.683 |
| Fz | α | 9 | 40.244 |
| C3 | θ | 10 | 47.561 |
| Fz | γ | 11 | 47.561 |
| Cz | θ | 12 | 51.220 |
| Fz | β | 13 | 50.000 |
| Fz | Amplitude | 14 | 53.659 |
| C4 | θ | 15 | 48.780 |
| C4 | γ | 16 | 47.561 |
| C3 | β | 17 | 47.561 |
| Cz | γ | 18 | 47.561 |
| C3 | δ | 19 | 46.341 |
| C3 | Amplitude | 20 | 47.561 |
| C4 | α | 21 | 46.341 |
| Fz | θ | 22 | 43.902 |
| C4 | Amplitude | 23 | 42.683 |
| C4 | δ | 24 | 42.683 |

Highest differentiation accuracy at "56.098%" when using 5 features from ranking 1 to 5

Pain context effect of same high temperature stimulation (brainwave amplitude)

Psychological stress paradigm

Cognitive task: Stroop color task (cognitive competitive task)

Font color task: answer "font color"
3 blocks (50 runs each)

Application of latent psychological degree of unpleasantness differentiation instrument (sigmoid function):

FIG.19

Procedures:

Feature extraction

1. Electrode extraction: virtual EOG electrode (main component analysis) is added to four electrodes at Fp1, Fp2, F3, and F4.
2. Blinking (EOG) removal: Extraction of EOG component (first component) by main component analysis → apply a regression filter on original data.
3. Reduction of myogenic potential (EMG): apply a 30 Hz high-cut filter.
4. Sample and "convert" brainwave from 5 seconds to 15 seconds after application of stimulation at level 1 (40°C) and level 6 (50°C) into absolute values (2 × 3 stimulations = 6 epochs).
5. "Convert into z values" using a rest segment (30 seconds before application of stimulation).

Amplification/replication of feature

6. Actually measured sample 1:
"Moving average" is multiplied while shifting a 5 second segment by 1 point each.
For each level, "30003 samples (10001 samples × 3 stimulations)" are created.

Actually measured sample 2:
"30 samples" are created for each level without a point overlap in one second segments.
7. Normal random numbers or Pearson system random numbers are generated using a distribution property of an actually measured sample in each electrode, and a "self-replicated feature" for 10000 samples is amplified/created.
*A "sample amplification method" is a technique of dramatically increasing the sample size using the distribution property thereof when there are few samples.

Differentiation model creation and evaluation

8. An individual differentiation model is created by machine learning (determination of coefficients by LASSO and Bayesian optimization)
9. Generalization capability of a model is confirmed by using another sample.

FIG.20

Differentiation model creation and generalization procedure

Model creation
1. By using 20000 replicated samples of an individual (ID 185) as learning data, a hyperparameter ($\lambda$) of a logistic regression model is determined by LASSO and Bayesian optimization, and weighting coefficients of features (five amplitudes) and a model intercept are determined.
*20000 samples amplified using normal random numbers and Pearson system random numbers are used.

Model evaluation
2. Test data for the other 169 subjects are differentiated and estimated using the determined individual model.
*Absolute mean amplitude (converted to z-value at rest) from 5 to 15 seconds after application of stimulation for brainwave data of the same experimental design was used as the test data (3 stimulations × 2 levels × 169 subjects).

3. The mean correct answer rate for 169 subjects is deemed the differentiation accuracy of the model.

FIG.21

Subjective evaluation of thermal pain of 1 subject

Subject (ID 185) used in individual model creation hardly felt any pain until the thermal stimulation was 40°C to 46°C, but the degree of unpleasantness (unbearabe unpleasantness) of pain suddenly increased at level 5's 48°C, and the degree of unpleasantness reached the ceiling of the scale at level 6.

↑

Therefore, a pleasantness/unpleasantness differentiation model was created using the farthest conditions of level 1 and level 6.

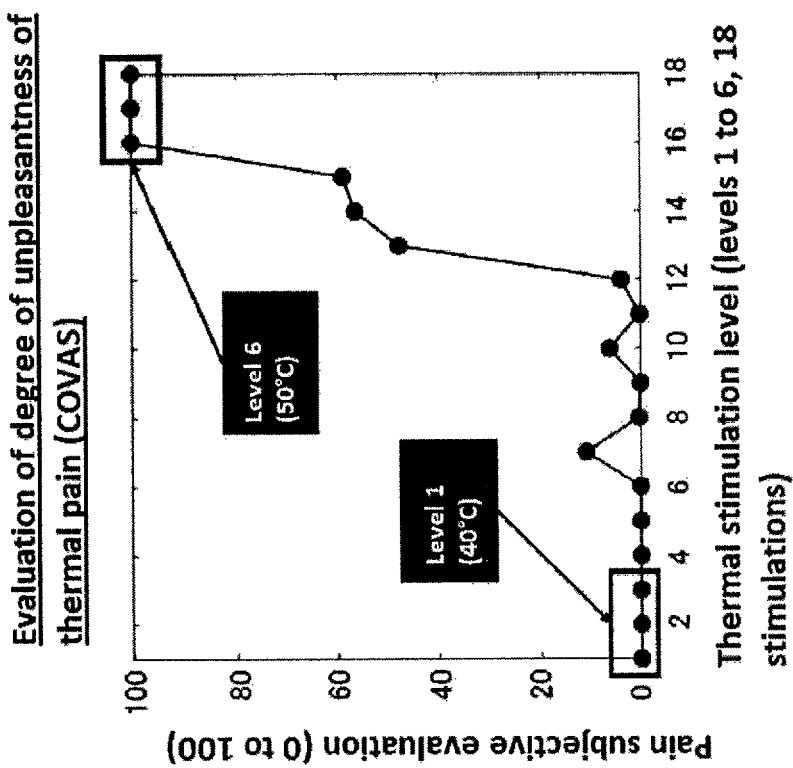

Evaluation of degree of unpleasantness of thermal pain (COVAS)

FIG.22
Sample distribution property of observed data (thermal stimulation levels 1 and 6)
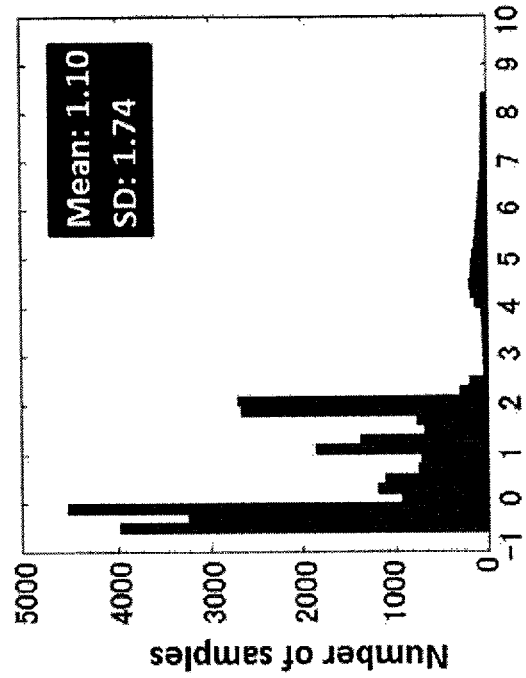
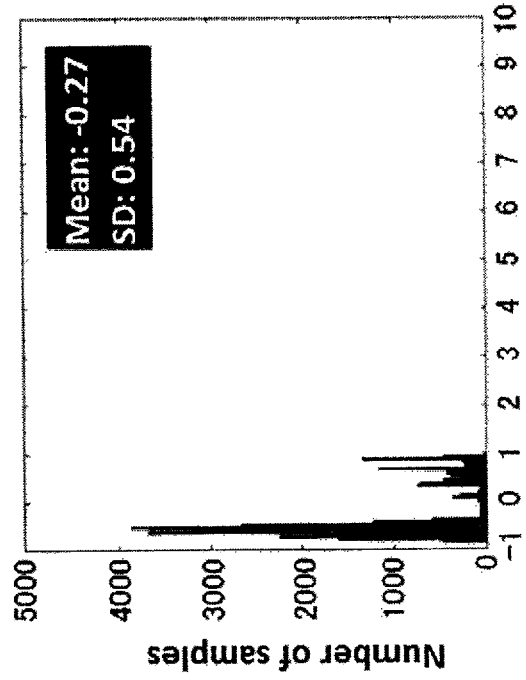
Distribution property for thermal stimulation level 6 extends to the right side in a wider range

DISCERNMENT OF COMFORT/DISCOMFORT

CROSS-REFERENCE TO RELATED APPLICATION

This application is a national stage application filed under 35 U.S.C. § 371, of International Patent Application No. PCT/JP2018/028300 filed Jul. 27, 2018, which claims the benefit of and priority to Japanese Application No. 2017-146553 filed Jul. 28, 2017; the contents of each of which are hereby incorporated by reference in their entirety.

TECHNICAL FIELD

The present invention relates to a technology for differentiating pleasantness/unpleasantness using a brainwave. More specifically, the present invention relates to differentiation of pleasantness/unpleasantness based on brainwave data or analysis data thereof from the same stimulation under different environments. For example, if there is pain, the present invention can differentiate whether the pain is comfortable pain or unpleasant pain.

BACKGROUND ART

Various sensations are often expressed as a unidirectional vector. For example, pain is often distinguished as whether pain is painful or not painful. However, painful sensation cannot be readily distinguished as to whether the pain is comfortable (pleasant) pain such as pain in acupuncture and moxibustion or unpleasant pain.

SUMMARY OF INVENTION

Solution to Problem

The inventors found a differentiation technology that can differentiate whether various sensations are comfortable (pleasant) sensations or unpleasant sensations.

The present invention provides, for example, the following.

(Item 1) A method of generating a device for determining stress or pleasantness/unpleasantness of an object, comprising:
a) applying the same stimulation to an object under at least two environments to obtain each brainwave data or analysis data thereof;
b) associating a difference in the brainwave data or analysis data thereof obtained under the at least two environments with a reaction of the object to the stimulation; and
c) generating a pleasantness/unpleasantness determination device for determining stress or pleasantness/unpleasantness of the object based on the association.

(Item 2) A method of determining stress or pleasantness/unpleasantness of an object, comprising:
a) applying the same stimulation to an object under at least two environments to obtain each brainwave data for a model or analysis data thereof;
b) associating a difference in the brainwave data for a model or analysis data thereof obtained under the at least two environments with a reaction of the object to the stimulation;
c) generating a pleasantness/unpleasantness determination device for determining stress or pleasantness/unpleasantness of the object based on the association; and
d) obtaining brainwave data for testing or analysis data thereof from the object and applying the data to the pleasantness/unpleasantness determination device to determine pleasantness/unpleasantness of the object.

(Item 3) A method of determining stress or pleasantness/unpleasantness of an object, comprising:
c) providing a pleasantness/unpleasantness determination device for determining stress or pleasantness/unpleasantness of an object based on association that is based on a test under at least two environments; and
d) obtaining brainwave data for testing or analysis data thereof from the object and applying the data to the pleasantness/unpleasantness determination device to determine pleasantness/unpleasantness of the object.

(Item 4) The method of any one of the preceding items, further comprising self-replicating the brainwave data for a model or analysis data thereof to increase the number of the brainwave data or analysis data thereof.

(Item 5) The method of any one of the preceding items, wherein the self-replication is performed based on a distribution property.

(Item 6) The method of any one of the preceding items, wherein the self-replication is performed by generating a normal random number or a Pearson system random number.

(Item 6A) The method of any one of the preceding items, wherein the self-replication is performed by generating a normal random number.

(Item 6B) The method of any one of the preceding items, wherein the self-replication is performed by generating a Pearson system random number.

(Item 7) The method of any one of the preceding items, wherein the association comprises setting a difference in pleasantness/unpleasantness and finding a feature related to the difference based on the environments and the stimulation, and generation of the pleasantness/unpleasantness determination device comprises affixing a label for distinguishing a difference in the stimulation using the feature.

(Item 8) The method of any one of the preceding items, wherein the generation of the pleasantness/unpleasantness determination device is achieved by sigmoid fitting or machine learning.

(Item 9) The method of any one of the preceding items, wherein, for the stress or pleasantness/unpleasantness, both stimulations applied to the object and the environments are different, stimulations applied to the object are different, but the environments are the same, or stimulations applied to the object are the same, but the environments are different.

(Item 10) The method of any one of the preceding items, wherein the stress or pleasantness/unpleasantness is from when the object is feeling pain.

(Item 11) The method of any one of the preceding items, wherein the pleasantness/unpleasantness determination device distinguishes an intensity of pain of the object from a level of stress or pleasantness/unpleasantness of the object.

(Item 12) The method of any one of the preceding items, wherein the brainwave data or analysis data thereof comprises at least one brainwave feature selected from:
Electrode position: positions on the scalp from a frontal portion to a parietal portion, and over an occipital position; positions in accordance with the international 10-20 system, or positions at a specific uniform distance; and
Time frame: 0 to 100, 100 to 200, 200 to 300, 300 to 400, 400 to 500, 500 to 600, 600 to 700, or 700 to 800 milliseconds (ms), or a combination of smaller time segments (10 milliseconds or the like) or longer time frames.

(Item 13) The method of any one of the preceding items, wherein the brainwave feature comprises at least one selected from the group consisting of Fp1, Fp2, Fpz, F3, F4, Fz, C3, C4, Cz, P3, P4, and Pz.

(Item 14) The method of any one of the preceding items, wherein the pleasantness/unpleasantness determination device materializes determination of pleasantness/unpleasantness with a negative potential level for a waveform during latency compared to a standard waveform.

(Item 15) The method of any one of the preceding items, wherein the negative potential level is based on a waveform in a range after 150 milliseconds from stimulation.

(Item 16) The method of any one of the preceding items, wherein the negative potential level is based on a waveform in a range after 300 milliseconds from stimulation.

(Item 17) The method of any one of the preceding items, wherein the negative potential level is based on a waveform in a range of 300 to 800 milliseconds after stimulation.

(Item 18) The method of any one of the preceding items, wherein the negative potential level is based on a negative occupancy in a range of 300 milliseconds to 800 milliseconds after stimulation.

(Item 19) The method of any one of the preceding items, wherein the pleasantness/unpleasantness determination device determines psychological stress.

(Item 20) An apparatus for generating a device or value for determining stress or pleasantness/unpleasantness of an object, comprising:
A) a data obtaining unit for applying the same stimulation to an object under at least two environments to obtain each brainwave data or analysis data thereof;
B) a processing unit for associating a difference in the brainwave data or analysis data thereof obtained under the at least two environments with a reaction of the object to the stimulation; and
C) a determination device generation unit for generating pleasantness/unpleasantness determination device or value for determining stress or pleasantness/unpleasantness of the object based on the association.

(Item 20A) The apparatus of item 20, further comprising a feature of any one or more of the preceding items.

(Item 21) An apparatus for determining stress or pleasantness/unpleasantness of an object, comprising:
A) a data obtaining unit for applying the same stimulation to an object under at least two environments to obtain each brainwave data for a model or analysis data thereof;
B) a processing unit for associating a difference in the brainwave data for a model or analysis data thereof obtained under the at least two environments with a reaction of the object to the stimulation;
C) a determination device provision unit for generating pleasantness/unpleasantness determination device or value for determining stress or pleasantness/unpleasantness of the object based on the association; and
D) a determination unit for obtaining brainwave data for testing or analysis data thereof from the object and applying the data to the pleasantness/unpleasantness determination device or value to determine pleasantness/unpleasantness of the object.

(Item 21A) The apparatus of item 21, further comprising a feature(s) of any one or more of the preceding items.

(Item 22) An apparatus for determining stress or pleasantness/unpleasantness of an object, comprising:
C) a determination device provision unit for providing a pleasantness/unpleasantness determination device or value for determining stress or pleasantness/unpleasantness of an object based on association that is based on a test under at least two environments; and
D) a determination unit for obtaining brainwave data for testing or analysis data thereof from the object and applying the data to the pleasantness/unpleasantness determination device to determine pleasantness/unpleasantness of the object.

(Item 22A) The apparatus of item 22, further comprising a feature of any one or more of the preceding items.

(Item 23) A program for implementing a method of generating a device for determining stress or pleasantness/unpleasantness of an object on a computer, the method comprising:
a) applying the same stimulation to an object under at least two environments to obtain each brainwave data or analysis data thereof;
b) associating a difference in the brainwave data or analysis data thereof obtained under the at least two environments with a reaction of the object to the stimulation; and
c) generating a pleasantness/unpleasantness determination device for determining stress or pleasantness/unpleasantness of the object based on the association.

(Item 23A) The program of item 23, further comprising a feature of any one or more of the preceding items.

(Item 24) A program for implementing a method of determining stress or pleasantness/unpleasantness of an object on a computer, the method comprising:
a) applying the same stimulation to an object under at least two environments to obtain each brainwave data for a model or analysis data thereof;
b) associating a difference in the brainwave data for a model or analysis data thereof obtained under the at least two environments with a reaction of the object to the stimulation;
c) generating a pleasantness/unpleasantness determination device for determining stress or pleasantness/unpleasantness of the object based on the association; and
d) obtaining brainwave data for testing or analysis data thereof from the object and applying the data to the pleasantness/unpleasantness determination device to determine pleasantness/unpleasantness of the object.

(Item 24A) The program of item 24, further comprising a feature of any one or more of the preceding items.

(Item 25) A program for implementing a method of determining stress or pleasantness/unpleasantness of an object on a computer, the method comprising:
c) providing a pleasantness/unpleasantness determination device for determining stress or pleasantness/unpleasantness of an object based on association that is based on a test under at least two environments; and
d) obtaining brainwave data for testing or analysis data thereof from the object and applying the data to the pleasantness/unpleasantness determination device to determine pleasantness/unpleasantness of the object.

(Item 25A) The program of item 25, further comprising a feature of any one or more of the preceding items.

(Item 26) A recording medium for storing a program for implementing a method of generating a device for determining stress or pleasantness/unpleasantness of an object on a computer, the method comprising:
a) applying the same stimulation to an object under at least two environments to obtain each brainwave data or analysis data thereof;
b) associating a difference in the brainwave data or analysis data thereof obtained under the at least two environments with a reaction of the object to the stimulation; and
c) generating a pleasantness/unpleasantness determination device for determining stress or pleasantness/unpleasantness of the object based on the association.

(Item 26A) The recording medium of item 26, further comprising a feature of any one or more of the preceding items.

(Item 27) A recording medium for storing a program for implementing a method of determining stress or pleasantness/unpleasantness of an object on a computer, the method comprising:

a) applying the same stimulation to an object under at least two environments to obtain each brainwave data for a model or analysis data thereof;
b) associating a difference in the brainwave data for a model or analysis data thereof obtained under the at least two environments with a reaction of the object to the stimulation;
c) generating a pleasantness/unpleasantness determination device for determining stress or pleasantness/unpleasantness of the object based on the association; and
d) obtaining brainwave data for testing or analysis data thereof from the object and applying the data to the pleasantness/unpleasantness determination device to determine pleasantness/unpleasantness of the object.

(Item 27A) The recording medium of item 27, further comprising a feature of any one or more of the preceding items.

(Item 28) A recording medium for storing a program for implementing a method of determining stress or pleasantness/unpleasantness of an object on a computer, the method comprising:

c) providing a pleasantness/unpleasantness determination device for determining stress or pleasantness/unpleasantness of an object based on association that is based on a test under at least two environments; and
d) obtaining brainwave data for testing or analysis data thereof from the object and applying the data to the pleasantness/unpleasantness determination device to determine pleasantness/unpleasantness of the object.

(Item 28A) The recording medium of item 28, further comprising a feature of any one or more of the preceding items.

The present invention is intended so that one or more of the aforementioned characteristics can be provided not only as the explicitly disclosed combinations, but also as other combinations thereof. Additional embodiments and advantages of the invention are recognized by those skilled in the art by reading and understanding the following detailed description as needed.

Advantageous Effects of Invention

The present invention can differentiate pleasantness/unpleasantness. The present invention can also differentiate pain between comfortable pain and unpleasant pain and administer more detailed therapy or surgery matching the subjective evaluation, so that the present invention is useful in the medicine related industries.

BRIEF DESCRIPTION OF DRAWINGS

FIG. 4 shows results of ranking of features in differentiation analysis by SVM-RFE. The differentiation accuracy was the highest when using the top five ranking features, exhibiting differentiation accuracy of "56.098%".

FIG. 19 shows an example of the procedure of Example 4.

FIG. 20 shows an example of differentiation model creation and generalization procedure of Example 4.

FIG. 21 shows an example of subjective evaluation of thermal pain of one subject, which is an example of creating a self-replicated feature by sample amplification for the creation of a pleasantness/unpleasantness differentiation model for each individual. The subject (ID 185) used in this Example hardly felt any pain until the thermal stimulation was 40° C. to 46° C., but the degree of unpleasantness (unbearable unpleasantness) of pain suddenly increased at level 5's 48° C., and the degree of unpleasantness reached the ceiling of the scale at level 6. Therefore, a differentiation model was created using the farthest conditions of level 1 and level 6.

FIG. 22 shows a sample distribution property of actual data (thermal stimulation levels 1 and 6). The left side shows the sample distribution (n=30003) for thermal stimulation level 1 (40° C.). The right side shows the sample distribution (n=30003) for thermal stimulation level 6 (50° C.). It can be understood that the distribution property for thermal stimulation level 6 extends to the right side in a wider range. In each graph, the y axis indicates the number of samples, and the x axis indicates the mean potential (absolute value, converted to z-value).

C.) at the Fp1 electrode had a mean: −0.27, SD: 0.7, skew: 1.90, and kurtosis: 6.22. The sample distribution (n=10000) for thermal stimulation level 6 (50° C.) at the Fp1 electrode had a mean: 1.21, SD: 3.15, skew: 3.44, and kurtosis: 15.97. A narrower area of overlap is advantageous for differentiation.

Figure 28:
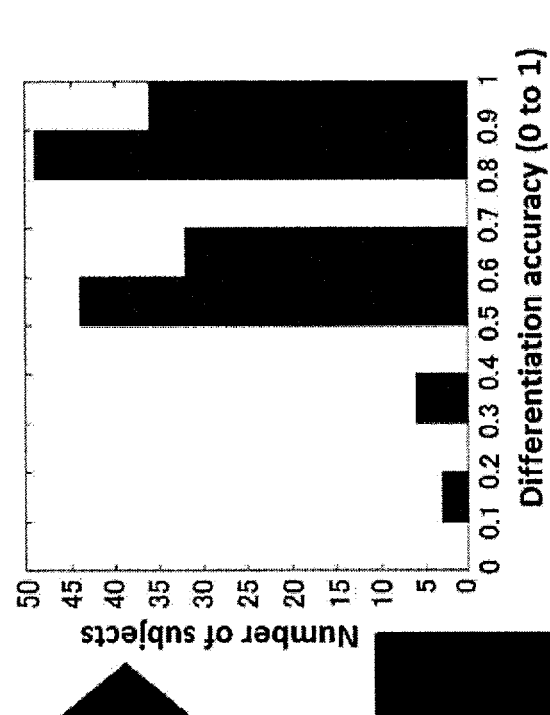

FIG. 28 shows a generalization example of an individual differentiation model (generalization 3; Pearson system random number amplification). A feature coefficient for an individual (ID 185) differentiation model was obtained, a differentiation model was determined, and level 1 and level pain differentiation and estimation was performed for different subjects (n=169). The estimation results was as follows: overall differentiation accuracy: 72.1% (SD 21.1), differentiation accuracy of 70 or greater: 84 subjects (49.7%), and differentiation accuracy of 50 or greater: 116 subjects (68.6%).

DESCRIPTION OF EMBODIMENTS

The present invention is explained hereinafter. Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. The terms used herein should also be understood as being used in the meaning that is commonly used in the art, unless specifically noted otherwise. Thus, unless defined otherwise, all terminologies and scientific technical terms that are used herein have the same meaning as the general understanding of those skilled in the art to which the present invention pertains. In case of a contradiction, the present specification (including the definitions) takes precedence.

Definition

The terms and the general technologies used herein are first explained.

As used herein, "object" is used synonymously with patient and subject and refers to any organism or animal which is subjected to the technology in the disclosure such as pain measurement and brainwave measurement. An object is preferably, but is not limited to, humans. As used herein, an object may be referred to as an "object being estimated" when estimating pain, but this has the same meaning as object or the like.

As used herein, "brainwave" has the meaning that is commonly used in the art and refers to a current generated by a difference in potential due to neurological activity of the brain when a pair of electrodes is placed on the scalp. Brainwave encompasses electroencephalogram (EEG), which is obtained from deriving and recording temporal changes in the current. A wave with an amplitude of about 50 μV and a frequency of approximately 10 Hz is considered the primary component at rest. This is referred to as an α wave. During mental activity, α waves are suppressed and a fast wave with a small amplitude of 17 to 30 Hz appears, which is referred to as a β wave. During a period of shallow sleep, α waves gradually decrease and Α waves of 4 to 8 Hz appear. During a deep sleep, δ waves of 1 to 4 Hz appear. These brainwaves can be expressed by a specific amplitude and frequency. In this present invention, analysis of amplitudes can be important.

As used herein, "brainwave data" is any data related to brainwaves (also referred to as "amount of brain activity", "brain feature", or the like), such as amplitude data (EEG amplitude, frequency property, or the like). "Analysis data" from analyzing such brainwave data can be used in the same manner as brainwave data, so that such data can be collectively referred to as "brainwave data or analysis data thereof" herein. Examples of analysis data include mean amplitude and peak amplitude (e.g., Fz, Cz, C3, C4), frequency power (e.g., Fz(δ), Fz(θ), Fz(α), Fz(β), Fz(γ), Cz(δ), Cz(θ), Cz(α), Cz(β), Cz(γ), C3(δ), C3(θ), C3(α), C3(β), C3(γ), C4(δ), C4(θ), C4(α), C4(β), and C4(γ)) and the like of brainwave data. Of course, this does not exclude other data commonly used as brainwave data or analysis data thereof.

As used herein, "amplitude data" is one type of "brainwave data" and refers to data for amplitudes of brainwaves. This is also referred to as simply "amplitude" or "EEG amplitude". Since such amplitude data is an indicator of brain activity, such data can also be referred to as "brain activity data", "amount of brain activity", or the like. Amplitude data can be obtained by measuring electrical signals of a brainwave and is indicated by potential (can be indicated by μV or the like). Amplitude data that can be used include, but are not limited to, mean amplitude.

As used herein, "frequency power" expresses frequency components of a waveform as energy and is also referred to as power spectrum. Frequency power can be calculated by extracting and calculating frequency components of a signal embedded in a signal contained in noise within a time region by utilizing fast Fourier transform (FFT) (algorithm for calculating discrete Fourier transform (DFT) on a computer at high speeds). Using the function periodgram in MATLAB, FFT on a signal can normalize the output thereof and calculate the power spectrum density PSD or power spectrum, which is the measurement of source of power. PSD indicates how power of a time signal is distributed with respect to frequencies. The unit thereof is watt/Hz. Each point in PSD is integrated over the range of frequencies where the point is defined (i.e., over the resolution bandwidth of PSD) to calculate the power spectrum. The unit of a power spectrum is watt. The value of power can be read directly from power spectrum without integration over the range of frequencies. PSD and power spectrum are both real numbers, so that no phase information is included. In this manner, frequency power can be calculated with a standard function in MATLAB.

As used herein, "pleasant (or pleasantness)" or "unpleasant (or unpleasantness)" is one of the most basic mental attributes for understanding behavior. This is an attribute which is a tendency to approach stimulation resulting in pleasantness, but to stay away from stimulation resulting in unpleasantness. Animals approach to acquire stimulation resulting in pleasantness, but behave in a way to avoid stimulation resulting in unpleasantness, evade stimulation that maintains an unpleasant state, or obtain stimulation that cancels the unpleasant state. Such behaviors to approach, avoid, and evade are fundamental behavioral principles for adapting to the environment and improving the likelihood of survival.

In this manner, "pleasantness" and "unpleasantness" are opposing concepts.

As used herein, "stress" refers to stress resulting from strain on the mind and body due to a burden on the mind and body from various external stimulations (stressor). Stress induces a disorder in the mind and body, such as insomnia, depression, stomach ache or headache, or stomach/duodenal ulcer. Stress includes pleasant stress and unpleasant stress. As used herein, stress is used synonymously with pleasantness/unpleasantness. Stress can be classified into "physical stress" and "mental stress". "Physical stress" can be classified into "external stress" resulting from external stimulation, and "internal stress" resulting from the inside of oneself under a specific environment. "Mental stress" can be classified into "social stress" induced during a social life and "psychological stress" induced from the psychological aspect of oneself. A psychological paradigm as used herein is a testing method set up to feel current and latent psychological stress in accordance with the personality or psychological state of an object when the object is placed under a specific environment.

As used herein, "pain" refers to a sensation that is generated as stimulation, generally upon intense injury such as damage/inflammation to a body part. In humans, pain is encompassed by common sensations as a sensation accompanying strong unpleasant feeling. In addition, cutaneous pain and the like also has an aspect as an external receptor to a certain degree, which plays a role in determining the quality such as hardness, sharpness, hotness (thermal pain), coldness (cold pain), or spiciness of an external object in cooperation with other skin sensation or taste. The sensation of pain of humans can occur at almost any part of the body (e.g., pleura, peritoneum, internal organs (visceral pain, excluding the brain), teeth, eyes, ears, and the like) other than the skin and mucous membrane, which can all be sensed as a brainwave or a change thereof in the brain. Additionally, internal sensation of pain represented by visceral pain is also encompassed by sensation of pain. The aforementioned sensation of pain is referred to as somatic pain relative to visceral pain. In addition to somatic pain and visceral pain, sensation of pain called "referred pain", which is a phenomenon where pain is perceived at a surface of a site that is different from a site that is actually damaged, is also reported. The present invention can classify such various pain types from the viewpoint of pleasantness/unpleasantness.

For sensation of pain, there are individual differences in sensitivity (pain threshold), as well as qualitative difference due to a difference in the receptor site or how a pain stimulation occurs. Sensation of pain is classified into dull pain, sharp pain, and the like, but sensation of pain of any type can be measured, estimated, and classified in this disclosure. The disclosure is also compatible with fast sensation of pain (A sensation of pain), slow sensation of pain (B sensation of pain), (fast) topical pain, and (slow) diffuse pain. The present invention is also compatible with abnormality in sensation of pain such as hyperalgesia. Two nerve fibers, i.e., "Aδ fiber" and "C fiber", are known as peripheral nerves that transmit pain. For example, when a hand is hit, the initial pain is transmitted as sharp pain from a clear origin (primary pain: sharp pain) by conduction through the Aδ fiber. Pain is then conducted through the C fiber to feel throbbing pain (secondary pain; dull pain) with an unclear origin. Pain is classified into "acute pain" lasting 4 to 6 weeks or less and "chronic pain" lasting 4 to 6 weeks or more. Pain is an important vital sign along with pulse, body temperature, blood pressure, and breathing, but is difficult to express as objective data. Representative pain scales VAS (Visual Analogue Scale) and faces pain rating scale are subjective evaluation methods that cannot compare pain between patients. Meanwhile, the inventors have focused on brainwaves which are hardly affected by the peripheral circulatory system as an indicator for objectively evaluating pain, arriving at the conclusion that pain types (pleasantness/unpleasantness) can also be classified by observing the change during latency/amplitude in response to pain stimulation. Instantaneous stimulation and persistent stimulation can also be classified in this manner.

One of the important points of the present invention is in the ability to distinguish whether pain is pain "requiring therapy" (unpleasant pain), rather than the intensity in itself. Therefore, it is important that "pain" can be clearly categorized with respect to the concept of "therapy".

As used herein, "subjective pain sensation level" refers to the level of sensation of pain of an object, and can be expressed by conventional technology such as computerized visual analog scale (COVAS) or other known technologies such as Support Team Assessment Schedule (STAS-J), Numerical Rating Scale (NRS), Faces Pain Scale (FPS), Abbey pain scale (Abbey), Checklist of Nonverbal Pain Indicators (CNPI), Non-communicative Patient's Pain Assessment Instrument (NOPPAIN), Doloplus 2, or the like.

As used herein, "condition" refers to an element that is a basis for establishing or inducing a certain matter, which is not the cause thereof, but places a restriction thereon. As used herein, a condition includes "stimulation" and "environment".

As used herein, "stimulation" refers to anything that causes some type of a reaction to an object. If the object is an organism, stimulation refers to a factor resulting in a temporary change in the physiological activity of the organism or a portion thereof. Although not wishing to be bound by any theory, for example the "environment" spatially encompasses an object without exerting any direct focused action (e.g., physical stimulation to a body part), whereas "stimulation" exerts such an action on the object.

Events related to sensation of pain presented as specific examples of "stimulation" include any stimulation that can cause sensation of pain. Examples thereof include electrical stimulation, cold stimulation, thermal stimulation, physical stimulation, chemical stimulation, and the like. In the present invention, stimulation can be any stimulation. Evaluation of stimulation can be matched with subjective pain sensation levels using, for example, conventional technology such as computerized visual analog scale (COVAS) or other known technologies such as Support Team Assessment Schedule (STAS-J), Numerical Rating Scale (NRS), Faces Pain Scale (FPS), Abbey pain scale (Abbey), Checklist of Nonverbal Pain Indicators (CNPI), Non-communicative Patient's Pain Assessment Instrument (NOPPAIN), Doloplus 2, or the like. Examples of values that can be employed as stimulation intensity include nociceptive threshold (threshold for generating neurological impulses in nociceptive fiber), pain detection threshold (intensity of nociceptive stimulation that can be sensed as pain by humans), pain tolerance threshold (strongest stimulation intensity among nociceptive stimulation that is experimentally tolerable by humans), and the like.

For psychological conditions, stimulation can be sensed by, for example, the five senses (sight, hearing, taste, touch, and smell). Examples thereof include any factor that is processed as information in the brain, any factor that can be mentally sensed such as social stress, and the like.

As used herein, "context" and "environment" are used in the same meaning, which is one type of condition referring to any condition surrounding an object that does not exert any direct focused action on the object. Context also refers to the surrounding circumstance when applying stimulation to an object. For example, in terms of the space where an object is placed, this refers to a three-dimensional space determined by various parameters defining a spatial property such as the temperature, humidity, density, brightness, size, slope, or height. At the physical level, clothing or accessories can also be understood as a parameter defining the body space. As seen in persons using a wheelchair, body space can be extended to the external environment. It was elucidated for the first time in the present invention that pleasantness/unpleasantness is sensed differently depending on the difference in the environment under which the object is placed or the context of the application of stimulation received by the object in addition to the fundamental circumstances of different stimulation resulting in a different degree of unpleasantness, and this can be presented as a signal analysis result.

As used herein, pleasantness/unpleasantness can be "classified" from various points of view (e.g., sensation of pain and psychological aspect). Representative examples include classification of whether pain of an object is "pleasant" or "unpleasant", but a methodology of classifying into "bearable" pain and "unbearable" pain can also be envisioned.

As used herein, "negative effect" refers to potential activity under a test condition of interest shifting in the minus direction relative to the potential activity under a comparative standard condition. As used herein, this refers to a shift of potential in the negative direction when there is current or latent stress compared to a state without a standard stress. On the other hand, an increase in positive potential is used as an indicator when the interest of the test is in a stress free state. The terms negative effect and positive effect are changed depending on the setting of the standard condition of a test.

As used herein, "negative occupancy" or "occupancy" is calculated by total time for negative potential (or number of data points for negative potential)/overall time (or total number of data points)×100. It was found that occupancy is an indicator of psychological stress. In this regard, 300 to 800 milliseconds after stimulation can be typically used as the time, but this is not a limiting example. Time can refer to a range after 150 milliseconds from stimulation, range after 300 milliseconds from stimulation, range of 300 milliseconds to 800 milliseconds from stimulation, range of 300 milliseconds to 600 milliseconds from stimulation, or the like. Occupancy is similar to duration of potential effect, but is suitable for expressing a temporal property of an effect when the effect is lost in the middle but immediately restarts. For 300 to 600 milliseconds described above, a positive potential effect is observed when conscious decision or the like converges, but a negative effect is observed persistently in cases of high burden in the cognitive task or continued suppressive function. Thus, there is an objective basis for use as an indicator of psychological stress (King J W, Kutas M. "Who did what and when? Using word- and clause-level ERPs to monitor working memory usage in reading." "J. Cogn. Neurosci. 7(3): 376-395, 1995).

As used herein, "self-replication" refers to replication of a number of sample or data based on the original data. The number of samples would dramatically increase as a result of self-replication. Self-replication can be materialized, for example, by generating random numbers such as normal random numbers or Pearson system random number amplification by using the distribution property of a sample (mean, SD). For example, a "self-replicated feature" of 10000 samples can be generated. Any multiple such as 10 samples, 50 samples, 100 samples, 500 samples, 1000 samples, 5000 samples, 10000 samples, 20000 samples, 50000 samples, or 100000 samples can be used for the amount of replication. Therefore, self replication is also referred to as a "sample amplification method". A "sample amplification method" is a technique of dramatically increasing the sample size using the distribution property thereof when there are few samples. For example, event-related potential used in the Examples generally uses a relatively small number of stimulation applications such as 20, 30, 40, 50, or 100 times, but this is only one brainwave data for one electrode if arithmetic mean is calculated. However, 20 brainwave data for one electrode obtained by applying stimulation 20 times can be theoretically amplified unlimitedly based on the distribution properties thereof (mean, degree of dispersion, kurtosis, skew) by using the sample amplification method of the invention. A hyperparameter (lambda, Cost, γ) of a differentiation model can be determined by machine learning (e.g., LASSO regularization or SVM in this Example) thereon, and weighting coefficients for features (e.g., 5 amplitudes) and a model intercept can be determined.

Preferred Embodiments

The preferred embodiments of the present invention are described hereinafter. It is understood that the embodiments provided hereinafter are provided to facilitate better understanding of the present invention, so that the scope of the invention should not be limited by the following descriptions. Thus, it is apparent that those skilled in the art can refer to the descriptions herein to make appropriate modifications within the scope of the invention. It is also understood that the following embodiments of the invention can be used individually or as a combination.

Each of the embodiments described below provides a comprehensive or specific example. The numerical values, shapes, materials, constituent elements, positions of arrangement and connection forms of the constituent elements, steps, order of steps, and the like in the following embodiments are one example, which is not intended to limit the Claims. Further, the constituent elements in the following embodiments that are not recited in the independent claims showing the most superordinate concept are described as an optional constituent element.

(Pleasantness/Unpleasantness Classification Method)

In one aspect, the present invention provides a method of generating a device or a determination value (this is a mathematical equation model using a function referred to as kernel when creating a determination instrument or a classification instrument in machine learning or the like; a classification label and feature are inputted therein to determine a parameter; an estimation value generated by this model is categorized ("1", "0", or the like) with a threshold value, i.e., classifier, and collated with an actual classification label to calculate differentiation accuracy; thus, the device or mathematical equation model and classifier have a relationship of a process and a result) for determining stress or pleasantness/unpleasantness of an object, comprising: a) applying the same stimulation, or stimulation with the same degree of intensity or the like, to an object under at least two environments to obtain each brainwave data or analysis data thereof; b) associating a difference in the brainwave data or analysis data thereof obtained under the at least two environments with a reaction of the object to the stimulation; and c) generating a pleasantness/unpleasantness determination device for determining stress or pleasantness/unpleasantness of the object based on the association.

In another aspect, the present invention also provides a method comprising-all of the stages from "determination value (device)" generation to "actual determination". Specifically, the present invention provides a method of determining stress or pleasantness/unpleasantness of an object, comprising: a) applying the same stimulation, or stimulation with the same degree of intensity or the like, to an object under at least two environments to obtain each brainwave data for a model or analysis data thereof; b) associating a difference in the brainwave data for a model or analysis data thereof obtained under the at least two environments with a reaction of the object to the stimulation; c) generating a pleasantness/unpleasantness determination device for determining stress or pleasantness/unpleasantness of the object based on the association; and d) obtaining brainwave data for testing or analysis data thereof from the object and applying the data to the pleasantness/unpleasantness determination device to determine pleasantness/unpleasantness of the object.

In another aspect, the present invention provides a method comprising a stage of implementation into a medical device while a "determination value" is already outputted. Specifically, the present invention provides a method of determining stress or pleasantness/unpleasantness of an object, comprising: c) providing a pleasantness/unpleasantness determination device for determining stress or pleasantness/unpleasantness of an object based on association that is based on a test under at least two environments; and d) obtaining brainwave data for testing or analysis data thereof from the object and applying the data to the pleasantness/unpleasantness determination device to determine pleasantness/unpleasantness of the object.

In another aspect, the present invention provides an apparatus for generating a device or value for determining stress or pleasantness/unpleasantness of an object, comprising: A) a data obtaining unit for applying the same stimulation, or stimulation with the same degree of intensity or the like, to an object under at least two environments to obtain each brainwave data or analysis data thereof; B) a processing unit for associating a difference in the brainwave data or analysis data thereof obtained under the at least two environments with a reaction of the object to the stimulation; and C) a determination device generation unit for generating a pleasantness/unpleasantness determination device or value for determining stress or pleasantness/unpleasantness of the object based on the association. A), B), and C) of the invention are configured to materialize steps a), b), and c), respectively.

In another aspect, the present invention provides an apparatus for determining stress or pleasantness/unpleasantness of an object, comprising: A) a data obtaining unit for applying the same stimulation, or stimulation with the same degree of intensity or the like, to an object under at least two environments to obtain each brainwave data for a model or analysis data thereof; B) a processing unit for associating a difference in the brainwave data for a model or analysis data thereof obtained under the at least two environments with a reaction of the object to the stimulation; C) a determination device provision unit for generating a pleasantness/unpleasantness determination device or value for determining stress or pleasantness/unpleasantness of the object based on the association; and D) a determination unit for obtaining brainwave data for testing or analysis data thereof from the object and applying the data to the pleasantness/unpleasantness determination device or value to determine pleasantness/unpleasantness of the object. A), B), C), and D) of the invention are configured to materialize steps a), b), c) and d), respectively.

In another aspect, the present invention provides an apparatus for determining stress or pleasantness/unpleasantness of an object, comprising: C) a determination device provision unit for providing a pleasantness/unpleasantness determination device or value for determining stress or pleasantness/unpleasantness of an object based on association that is based on a test under at least two environments; and D) a determination unit for obtaining brainwave data for testing or analysis data thereof from the object and applying the data to the pleasantness/unpleasantness determination device to determine pleasantness/unpleasantness of the object. C) and D) of the invention are configured to materialize steps c) and d), respectively.

The stimulation function in A) can have a device or function capable of providing a plurality of types of stimulation intensities. The function is configured to be able to apply such stimulation to an object. The function for obtaining brainwave data (e.g., amplitude data) in A) is configured to obtain brainwave data of an object. A) can materialize these two functions as separate parts or as an integral part. A) can also have other functions.

B) has a function for analyzing the association of measurement results with a difference in two or more contexts (environments) and any function fitting such as sigmoid curve fitting.

C) can have a function for generating a pleasantness/unpleasantness determination device or value.

D) can have a function for obtaining brainwave for measurement or the like and fitting this to the pleasantness/unpleasantness determination device or value obtained in C) to determine pleasantness/unpleasantness.

At least two of the functions A), B), C), and D) can be materialized with another apparatus, device, CPU, terminal, or the like, or as a single part. Generally, the function is configured to be incorporated, or configured to be capable of being incorporated into a program that materializes such calculation in a single CPU or computer.

Each step is described hereinafter.

Figure 15:
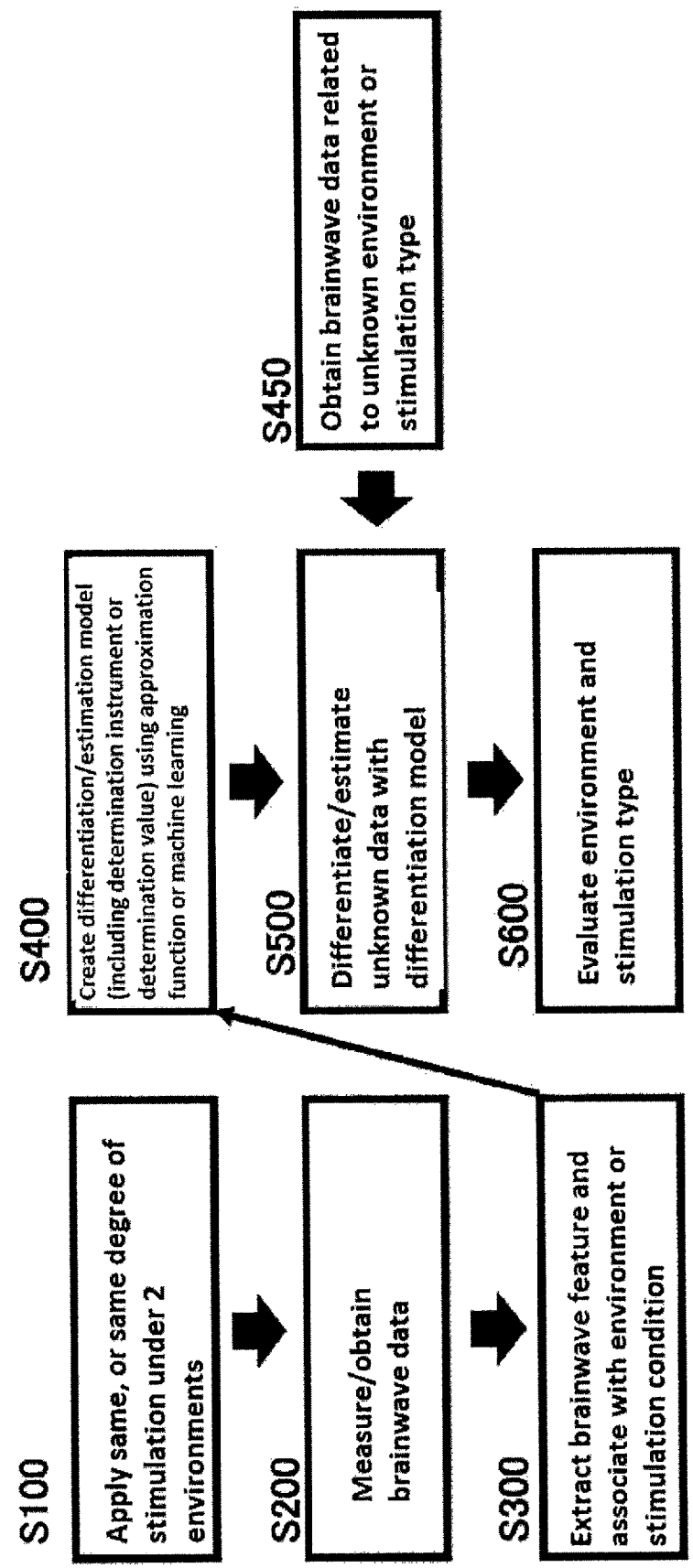
FIG. 15 is an example of a flowchart showing the flow of the invention.

A pleasantness/unpleasantness methodology is described hereinafter using a schematic diagram (FIG. 15).

Regarding step a) applying the same stimulation, or stimulation with the same degree of intensity or the like, to an object under at least two environments to obtain each brainwave data for a model or analysis data thereof (S100 to S200):

This step applies the same (or same type of) stimulation, or stimulation of the same degree (e.g., pain stimulation) a plurality of times to an object under at least two environments (preferably different environments) to measure or obtain each brainwave data for a model or analysis data thereof. Alternatively, the step of stimulating the object being estimated with a plurality of levels of stimulation intensities (S100) applies stimulation selected from a plurality of levels (strength or magnitude) of a plurality of stimulations (e.g., cold temperature stimulation, electrical stimulation, or the like) to an object being estimated, and obtains brainwave data (also referred to as brain activity data, amount of brain activity, or the like (S100) including, for example, amplitude data (EEG amplitude), frequency property, and the like) of the object being estimated corresponding to the stimulation intensity (S200). Such brainwave data can be obtained using any methodology that is well known in the art. Brainwave data can be obtained by measuring electrical signals of a brainwave and is displayed by potential (can be displayed by μV or the like) as amplitude data or the like. Frequency properties are displayed as power spectrum density or the like.

In a preferred embodiment, brainwave data is preferably collected by a simple method, which can 1) use minimum number of electrodes (about 2), 2) avoid the scalp with hair as much as possible, and 3) record while sleeping, to carry out the invention. The number of electrodes can be increased as need (e.g., 3, 4, 5, or the like).

Alternatively, the brainwave data for a model or analysis data thereof (e.g., event-related potential or evoked potential in this Example) can be self-replicated to increase the number of the brainwave data or analysis data thereof. Self-replication can be performed based on a distribution property. Self-replication can also be performed by generating a random number such as a normal random number or a Pearson system random number. Alternatively, self-replication can generate normal random numbers using the distribution property of a sample (mean, standard deviation (SD)) to amplify and create a "self-replicated feature" of a suitable number of samples (e.g., 10000, 20000, or the like). A "sample amplification method" can be considered as a technique of dramatically increasing the sample size using the distribution property thereof even when there are few samples.

Regarding b) associating a difference in the brainwave data for a model or analysis data thereof obtained under the at least two environments with a reaction of the object to the stimulation (S300):

A difference in brainwave data or analysis data thereof obtained as in a) is associated with a condition parameter (e.g., degree of unpleasantness of pain stimulation or the like) comprising a parameter related to stimulation and environment such as a stimulation type or stimulation application environment based on an appropriate methodology.

S300 is a step of setting a difference in pleasantness/unpleasantness based on a difference in conditions (or stimulation) or a difference in environments (or context) and finding a feature associated therewith.

S400 is a step for labeling a difference in conditions and performing sigmoid fitting, machine learning, or the like using the feature. More specifically, the step is as follows.

The procedure related to the degree of unpleasantness or the procedure for associating a difference in the environments with a brainwave feature in S300 is performed, for example, in the following manner. If there are similar environments A and B with different degrees of unpleasantness in a normal environment, factors related to environmental configurations are listed as much as possible. The factors are statistically compared between environments A and B to examine whether there is a significant difference. If a significant difference is found, the factor is considered a likely candidate associated with the difference in the degrees of unpleasantness in environments A and B. A brainwave feature has a temporal, spatial, or complex property comprised of the interaction thereof, such as amplitude, latency, persistent period of effect, distribution, or frequency power. Thus, there is no guarantee that a feature associated with a difference between environments A and B is intuitively found. Therefore, a feature is temporally and spatially analyzed and decomposed into parts to statistically compare features associated with environments A and B (t-test or analysis of variance) or study the continuous relationship (correlation or regression) to identify the relationship between stimulation or environmental conditions and features.

In this step, the brainwave data obtained in step a is subjected to basic signal processing such as filtering, eye movement correction, or artifact removal and then associated with a condition parameter, and a signal of a corresponding portion is extracted to create a brainwave feature (S300). This includes a mean value (arithmetic mean or geometric mean), other representative value (median or mode), entropy, frequency power, wavelet, mean, single run event related potential component, and the like.

Regarding c) generating a pleasantness/unpleasantness determination device for determining stress or pleasantness/unpleasantness of the object based on the association (S400):

This is a step of determining a threshold value or determination index on a model curve obtained by fitting using the brainwave feature associated with a conditional parameter related to an environment and stimulation calculated in b). A threshold value can be set with a numerical value such as a threshold value potential or (negative) occupancy and used as a determination index.

S400 creates a model for differentiating/estimating existing or unknown stimulation or environment using a feature identified by the association in S300. For example, with the statistical test on features described above, the possibility of determining that "there is a significant difference between conditions" increases if the number of samples increases, even if the number of samples with a small difference, no difference, or reversed difference between environments A and B is increased. However, the viewpoint of the extent to which the feature can differentiate a sample is not included. However, it is important that pain or stress sensed by an individual can be distinguished with as much accuracy as possible for differentiation of pain or psychological stress, so that effectiveness which is different from detection of statistically significant difference is required and intended.

A differentiation/estimation model is created for 2, 3, or more classifications in accordance with a conditional parameter using a brainwave feature. As one method, a plot diagram is created and fitted to an appropriate fitting function such as a sigmoid function pattern. Fitting can be performed using any methodology that is known in the art. Specific examples of such fitting functions include, but are not limited to, a Boltzmann function, double Boltzmann function, Hill function, logistic dose response, sigmoid Richards function, sigmoid Weibull function, and the like. A standard logistic function is particularly called a sigmoid function. A standard function or a modified form thereof is common and preferred.

If a regression coefficient for fitting to an appropriate function pattern such as the sigmoid function pattern is equal to or greater than a predetermined value, a threshold value for determining pleasantness/unpleasantness can be optionally determined based on the sigmoid curve or the like. In this regard, a threshold value can be generated based on an inflection point (modulation point) for a sigmoid curve, but this is not a limiting example. A pain classifier can be optionally calibrated to maximize the classification of levels of pleasantness/unpleasantness. A threshold value can be applied to calculation or classification of pleasantness/unpleasantness levels and used in determining a therapeutic effect.

Thus, in one specific embodiment, the association comprises setting a difference in pleasantness/unpleasantness and finding a feature related to the difference based on conditions such as the environments and the stimulation, and generation of the pleasantness/unpleasantness determination device comprises affixing a label for distinguishing a difference in the stimulation using the feature. In a specific embodiment, the generation of the pleasantness/unpleasantness determination device is achieved by sigmoid fitting or machine learning.

In one embodiment, for the stress or pleasantness/unpleasantness, 1) both stimulations applied to the object and the environments are different, 2) stimulations applied to the object are different, but the environments are the same, or 3) stimulations applied to the object are the same, but the environments are different. More specifically, 1) is based, for example, on a property where the type of stimulation applied and space in which stimulation is applied are different, and the difference is associated with the degree of unpleasantness. 2) is, for example, type of stimulation applied or intensity of stimulation is different while the context (environment) of application is different, which is associated with the difference in the degree of unpleasantness. 3) is, for example, the method of applying stimulation or detailed task is exactly the same, but the spatial property where an object is placed differs, which is associated with the difference in the degree of unpleasantness.

While an actual medical device can be configured to perform a) to c), a determination instrument or determination value can be set in advance. In such a case, step c) can be step c') for providing a pleasantness/unpleasantness determination device for determining stress or pleasantness/unpleasantness of an object based on association that is based on a test under at least two environments.

If the same subject is targeted, the step can comprise a step of succeeding or updating a determination instrument or determination value by using the previous pleasantness/unpleasantness determination device (value or the like).

Regarding d) obtaining brainwave data related to an unknown state for testing or analysis data thereof from the object (S450) and applying the data to the pleasantness/unpleasantness determination device to determine pleasantness/unpleasantness of the object (S500):

This step calculates, based on a determination instrument or a threshold value, a numerical value corresponding to the determination instrument or threshold value from a measurement value related to an unknown state of an object actually measured such as brainwave data or analysis data thereof and compares this value with the determination instrument of threshold value to determine the presence/absence of pleasantness/unpleasantness or the level thereof.

This is a step of obtaining brainwave data (e.g., amplitude data) of the object (S450). This is a step of obtaining brainwave data from an object in an unknown state from the object on which measurement is intended, regardless of whether some type of simulation or treatment is applied. Any methodology can be used as long as it is a methodology that can obtain brainwave data. The same methodology for obtaining brainwave data used in step a) can be used. Generally, the same methodology is used. As specified in S500, this is applied to a pleasantness/unpleasantness determination instrument or a determination value to determine pleasantness/unpleasantness of the object. A predetermined pleasantness/unpleasantness determination device or value is referred to as a "degree of unpleasantness (pleasantness/unpleasantness) determination instrument" or "degree of unpleasantness (pleasantness/unpleasantness) determination prediction instrument" in association with the level differentiated/estimated for an object. It is determined or predicted that there is unpleasantness with a numerical value more toward the unpleasantness side than the threshold value and determined or predicted that there is pleasantness with a numerical value on the pleasantness side.

In one embodiment, brainwave data (e.g., amplitude data) can be fitted to the pleasantness/unpleasantness determination device or value with a mean value. Such a mean value can be a mean value of 15 seconds to 200 seconds, or in excess of 200 seconds (e.g., 300 seconds, 500 seconds, 600 seconds, 900 seconds, 1200 seconds, or the like) when data record spans several hours. For event related brain activity synchronizing with an external or internal event in a short period of time (e.g., 1 second or less), this can be a mean value, representative value, chronological change data, or the like for 1 second or less after the occurrence of the event. Data used in a differentiation instrument or a determination value is desirably standardized or normalized. When data for different dates or times are compared, it is desirable to set a common baseline environment or stimulation type, and calculate the change or effect with respect thereto and associate the change or effect with a differentiation instrument or determination value. In one embodiment, the association can be materialized by using the sigmoid function as a differentiation instrument.

In another embodiment, unknown stress or pleasantness/unpleasantness to be differentiated/estimated is from when the object is feeling pain.

In still another embodiment, the physical intensity of "pain" and "stress (pleasantness/unpleasantness)" can be displayed with separate parameters. In this embodiment, a two-dimensional parameter can be produced. More specifically, the pleasantness/unpleasantness determination device distinguishes an intensity of pain of the object from a level of stress or pleasantness/unpleasantness of the object independent of physical intensity. In this regard, it was found that there is a parameter indicating stress or pleasantness/unpleasantness levels separate from a physical amount as a pain sensation for feeling pain or color perception for perceiving colors. While stimulation is the same or controlled to be the same as much as possible as an index other than a physical parametric intensity, such pleasantness/unpleasantness or stress indices can be calculated by changing the environment parameter affecting stress and degree of unpleasantness. Examples of these indices include occupancy in a specific time range of negative potential activity in a psychological paradigm and the like, but is based, as a premise thereof, on a property such as persistence of effective time or increase in amplitude due to an increase in the suppression function or cognitive burden (e.g., burden to remember tasks) for negative brainwave activity.

In one embodiment, the brainwave data or analysis data thereof comprises, as data recording positions, frontal-parietal portions such as F3, F4, C3, C4, P3, and P4 in compliance with the international 10-20 system or expanded standard thereof, and positions on the scalp over the occipital portion as electrode positions. Alternatively, positions at a specific uniform distance (e.g., 2.5 cm or the like) can be covered. The time frame of recording and analysis can be, for a short period of event related potential activity, 0 to 100, 100 to 200, 200 to 300, 300 to 400, 400 to 500, 500 to 600, 600 to 700, 700 to 800 milliseconds (ms), a shorter time segment (10 milliseconds or the like), or a longer time frame (sometimes spanning several seconds). The brainwave data or analysis data thereof comprises at least one brainwave feature selected from combinations thereof.

In still another embodiment, the brainwave feature comprises at least one selected from the group consisting of Fp1, Fp2, Fpz, F3, F4, Fz, C3, C4, Cz, P3, P4, and Pz, such as mean amplitudes Fz, C3, and C4, and frequencies Fz ($\delta$), Fz($\beta$), Cz($\delta$), C3($\theta$), and C4($\beta$). It is preferable that the feature comprises, but not limited to, Cz (amplitude), C3($\alpha$), Cz($\beta$), Fz($\delta$), and Cz($\gamma$).

Figure 16:
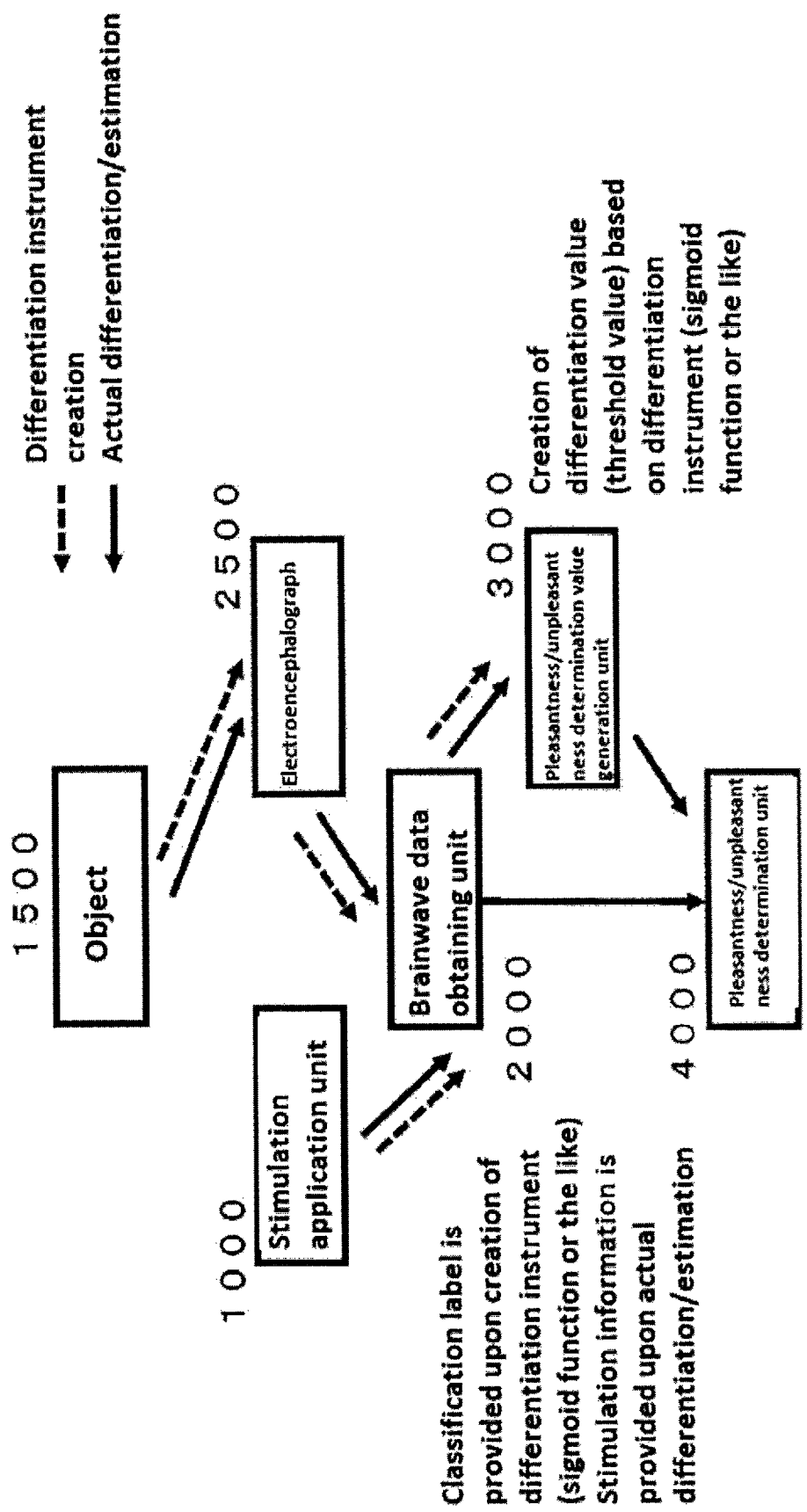
FIG. 16 is an example of a block diagram showing the function configuration of the invention.

FIG. 16 describes a schematic diagram of the apparatus of the invention. This embodiment involves 1000 to 3000 therein when generating a pleasantness/unpleasantness determination instrument (device). A stimulation application unit 1000 corresponds to A), where information related to the environment in which stimulation is applied or stimulation type is communicated to a brainwave data obtaining unit 2000 and a pleasantness/unpleasantness determination value generation unit 3000. The brainwave data obtaining unit 2000 is configured to comprise or to be connected to an electroencephalograph that is or can be connected to an object (1500), so that brainwave data synchronized with stimulation emitted from a stimulation application unit to the object (1500) is obtained (2500).

Figure 17:
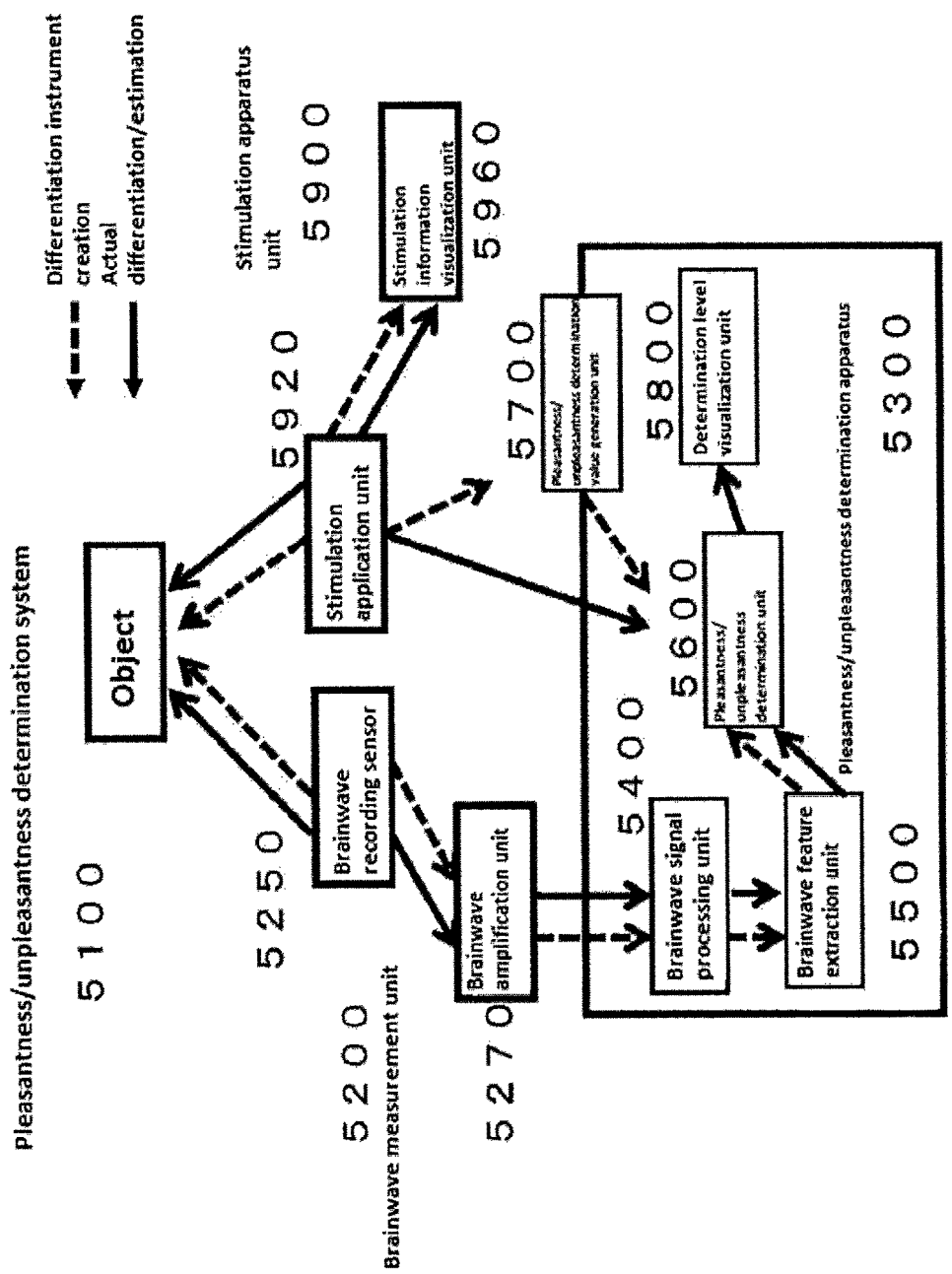
FIG. 17 is an example of a block diagram showing the function configuration of the invention.

FIG. 17 is a block diagram showing the functional configuration of a pleasantness/unpleasantness determination system 5100 in one embodiment (it should be noted that some of the configuration diagrams are optional constituents that can be omitted). The system 5100 comprises a brainwave measurement unit 5200, which internally comprises or externally connects to a brainwave recording sensor 5250 and optionally a brainwave amplification unit 5270. Signal processing and differentiation/estimation of pleasantness/unpleasantness is performed at a pleasantness/unpleasantness determination apparatus 5300. In the pleasantness/unpleasantness determination apparatus 5300, brainwave signals are processed at a brainwave signal processing unit 5400 (and a brainwave feature is extracted, sometimes amplified, at a brainwave feature extraction unit 5500 as needed), pleasantness/unpleasantness or degree of unpleasantness is differentiated/estimated at a pleasantness/unpleasantness determination unit 5600, and the degree of unpleasantness is (optionally) made visible at a differentiation level visualization unit 5800. The system also comprises a stimulation apparatus unit 5900 internally or externally. The stimulation apparatus unit 5900 transmits stimulation information (stimulation type, environment information, or the like) for differentiating actual unknown levels of degree of unpleasantness and creating a pleasantness/unpleasantness and unpleasantness differentiation instrument of an object. The stimulation apparatus unit 5900 comprises a stimulation application unit 5920 and optionally a stimulation information visualization unit 5960 to display information such as an image or number associated with stimulation or environment. The pleasantness/unpleasantness determination system can also comprise a generation unit 5700 for generating a differentiation instrument or a determination value externally or internally to the apparatus 5300.

Such a pleasantness/unpleasantness determination system 5100 comprises the brainwave measurement unit 5200 and the pleasantness/unpleasantness determination apparatus 5300, and optionally the stimulation apparatus unit 5900. The pleasantness/unpleasantness determination apparatus 5300 is materialized, for example, by a computer comprising a processor and a memory. In such a case, the pleasantness/unpleasantness determination apparatus 5300 makes a processor function optionally as the brainwave amplification unit 5270, brainwave signal processing unit 5400, (optionally) pleasantness/unpleasantness determination unit 5600, (optionally) differentiation level visualization unit 5800, and the like when a program stored in the memory is implemented by the processor. The stimulation or environmental information is also made visible as needed. The system 5100 or pleasantness/unpleasantness determination apparatus 5300 of the invention can be materialized for example, with a dedicated electrical circuit. A dedicated electrical circuit can be a single integrated circuit or a plurality of electrical circuits. A brainwave data obtaining unit and pleasantness/unpleasantness determination value generation unit can have the same configuration as the pleasantness/unpleasantness determination apparatus.

The measurement unit 5200 obtains a plurality of brainwave data by measuring a brainwave a plurality of times from an object being estimated via an electroencephalograph (brainwave recording sensor 5250). The object being estimated is an organism in which a change in brainwave is induced by stimulation or environment, which is not limited to humans.

The pleasantness/unpleasantness determination unit 5600 differentiates/estimates the degree of unpleasantness using a determination value. A differentiation instrument or determination value is also generated when not generated externally or internally in advance. A part generating a differentiation instrument or determination value can be comprised externally or internally to the apparatus 5300 as the pleasantness/unpleasantness determination value generation unit 5700. A degree of unpleasantness determination value is for estimating or classifying the degree of unpleasantness from amplitudes of a plurality of brainwave data. Specifically, the pleasantness/unpleasantness determination unit 5600 or the pleasantness/unpleasantness determination value generation unit 5700 can generate a determination value for estimating or classifying the degree of unpleasantness of an object from brainwave data.

The brainwave recording sensor 5250 measures electrical activity generated in the brain of an object being estimated with an electrode on the scalp. The brainwave recording sensor 5250 then outputs the result of measurement, i.e. brainwave data. Brainwave data can be amplified as needed.

This is further explained based on FIG. 16. The aspect comprising a determination unit is described. FIG. 16 references the brainwave data obtaining unit 2000 in addition to the pleasantness/unpleasantness determination unit 4000. The dotted lines indicate the procedure for creating a differentiation model, and the solid lines indicate the procedure for differentiating/estimating an actual pain level. In this case, as described in the section of (Generation of pleasantness/unpleasantness determination value), brainwave data can be obtained via an electroencephalograph from the object 1500. Specifically, the brainwave data obtaining unit 2000 is configured to be connectable to the object 1500, and the brainwave data obtaining unit 2000 is configured to comprise or to be connected to an electroencephalograph that is or can be connected to the object (1500), so that brainwave data obtained from the object (1500) can be obtained (2500). The pleasantness/unpleasantness determination unit 4000 is configured to store a pleasantness/unpleasantness determination value in advance or receive data generated separately, and optionally configured to be capable of referencing. Such a connection configuration can be wired or wireless connection. A pleasantness/unpleasantness determination value stored in advance is generated based on, for example, a differentiation instrument of a feature (sigmoid function fitting or the like) in the pleasantness/unpleasantness determination value generation unit 3000.

FIG. 17 is a block diagram showing the functional configurations of the pleasantness/unpleasantness determination system 5100 in one embodiment. The system 5100 comprises the brainwave measurement unit 5200, which internally comprises or externally connects to the brainwave recording sensor 5250 and optionally the brainwave amplification unit 5270. Signal processing and differentiation/estimation of pain are performed at the pleasantness/unpleasantness determination apparatus 5300. In the pleasantness/unpleasantness determination apparatus 5300, brainwave signals are processed at the brainwave signal processing unit 5400, pain is (optionally) differentiated/estimated at the pleasantness/unpleasantness determination unit 5600, and pain is (optionally) made visible at the differentiation level visualization unit 5800. The system also comprises the stimulation apparatus unit 5900 internally or externally. The stimulation apparatus unit 5900 contributes to the creation of a degree of unpleasantness differentiation instrument of an object. A determination value can be created in advance at the pleasantness/unpleasantness determination value generation unit 5700.

In this manner, the pleasantness/unpleasantness determination system 5100 comprises the brainwave measurement unit 5200 and the pleasantness/unpleasantness determination apparatus 5300. The pleasantness/unpleasantness determination apparatus 5300 is materialized, for example, by a computer comprising a processor and a memory. In such a case, the pleasantness/unpleasantness determination apparatus 5300 makes a processor function optionally as the brainwave amplification unit 5270, brainwave signal processing unit 5400, (optionally) pleasantness/unpleasantness determination unit 5600, (optionally) differentiation level visualization unit 5800, and the like when a program stored in the memory is implemented by the processor. Reference stimulation is also made visible and vocalized as needed. The system 5100 or apparatus 5300 of the invention can be materialized, for example, with a dedicated electrical circuit. A dedicated electrical circuit can be a single integrated circuit or a plurality of electrical circuits. A brainwave data measurement unit and pleasantness/unpleasantness determination value generation unit 3000 (see FIG. 16) can have the same configuration as the pain estimation apparatus or can be configured as an external unit.

The measurement unit 5200 obtains a plurality of brainwave data by measuring a brainwave a plurality of times from an object being estimated via an electroencephalograph (brainwave recording sensor 5250). The object being estimated is an organism in which a change in brainwave is induced by pain, which is not limited to humans.

The pleasantness/unpleasantness determination unit 5600 estimates or classifies the magnitude of pain from amplitudes of a plurality of brainwave data based on a pain classifier created by the pleasantness/unpleasantness determination value generation unit 3000 (see FIG. 16). Specifically, the pleasantness/unpleasantness determination unit 5600 estimates or classifies pain of an object from brainwave data based on a determination value.

The brainwave recording sensor 5250 measures electrical activity generated in the brain of an object being estimated with an electrode on the scalp. The brainwave recording sensor 5250 then outputs the result of measurement, brainwave data. Brainwave data can be amplified as needed.

Next, the process or method of an apparatus configured in the above manner is described. FIG. 15 is a flowchart showing a series of processing. In this aspect, S400 to S600 can be involved. This is a step after generating a degree of unpleasantness determination value (also referred to as a degree of unpleasantness determination instrument/degree of unpleasantness determination instrument) using stimulation or environment information (conditional parameter) at S400, or when a degree of pleasantness/unpleasantness determination value is available separately (when obtained and stored previously or the like).

A degree of unpleasantness determination value, after creation, can be stored in the pleasantness/unpleasantness determination unit 4000 in advance (see FIG. 16), or the pleasantness/unpleasantness determination unit 4000 can be configured to be able to receive value data. Alternatively, if the pleasantness/unpleasantness determination value generation unit 3000 is installed, the value can be stored in the generation unit. A recording medium can be provided separately. This value can also be received through communication.

Next, brainwave data is obtained from an object (S450) (see FIG. 15). The brainwave data can be obtained using the same technology as the explanation for S200. While the same embodiment can be employed, the same apparatus or device as S200 does not always need to be used, which can be the same or different.

Next, brainwave data (e.g., amplitude data) obtained in S450 is fitted to a degree of unpleasantness determination value, and the degree of unpleasantness corresponding to the brainwave data is differentiated/estimated (S500) (see FIG. 15). Such degree of unpleasantness determination can be configured so that a certain phrase (like, dislike, or the like) is displayed or vocalized when a predetermined value is outputted, and an actual value and a degree of unpleasantness determination value are displayed in juxtaposition to allow a user (clinician) to review the values.

Figure 18:
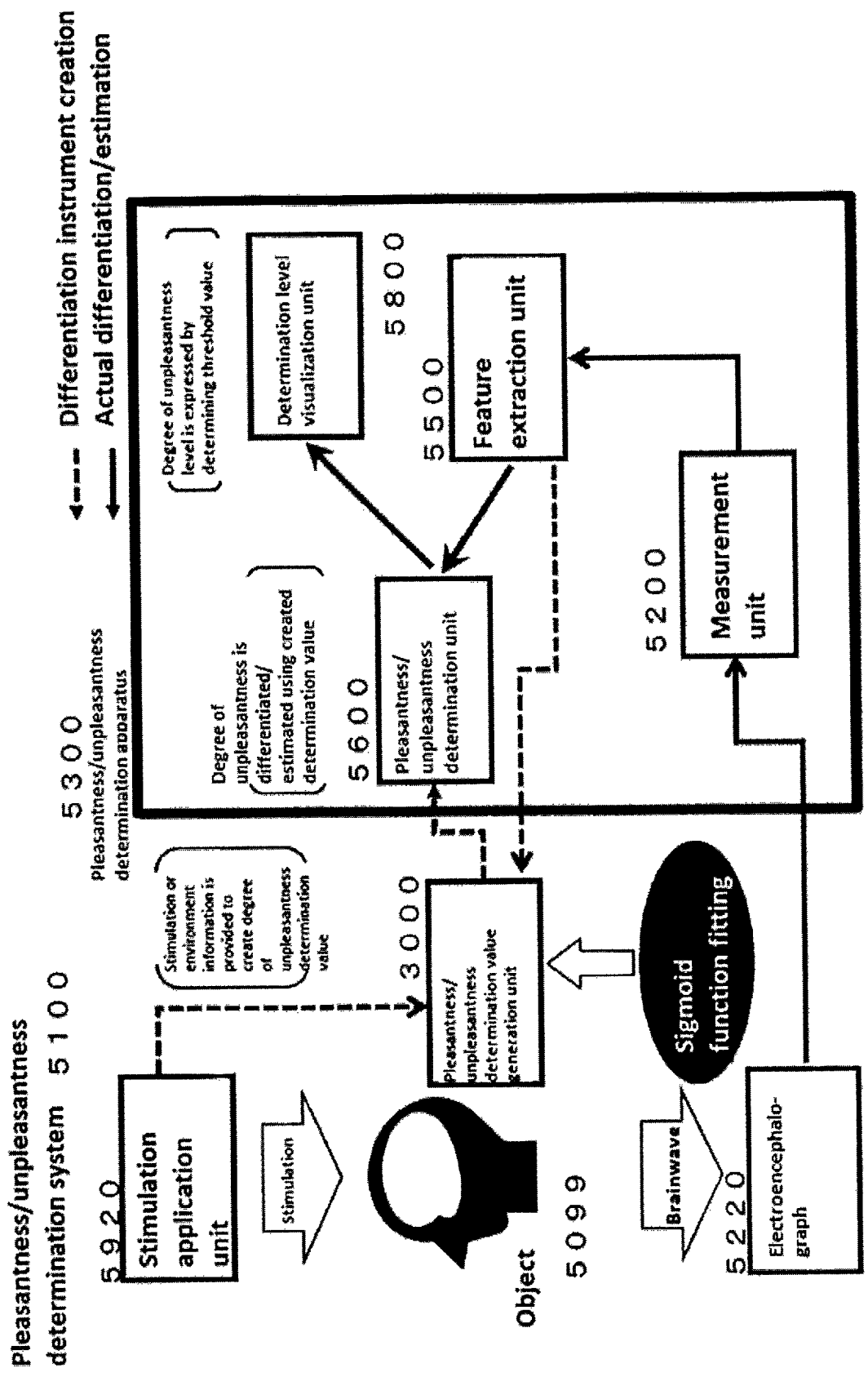
FIG. 18 is another example of a block diagram showing the function configuration of the invention.

FIG. 18 is a diagram of the pleasantness/unpleasantness determination system 5100 describing the details of the operation, extending the block diagram of FIG. 17 to include the process of generating a differentiation instrument (e.g., sigmoid function fitting). The system 5100 comprises the brainwave measurement unit 5200, is connected to the electroencephalograph 5220, obtains a brainwave feature such as a mean value at the feature extraction unit 5500 from the collected brainwave data as needed, and amplifies the sample. When a degree of unpleasantness determination value is generated in advance, a degree of unpleasantness determination value is generated by a differentiation instrument, e.g., sigmoid function fitting, at the pleasantness/unpleasantness determination value generation unit 3000 external or internal to the pleasantness/unpleasantness determination apparatus 5300. The determination value is transmitted to and stored in the pleasantness/unpleasantness determination unit 5600. In determining the degree of unpleasantness of actual unknown stimulation type or environment, brainwave data synchronized with the application or display of stimulation at the stimulation application unit 5920 is transmitted from the electroencephalograph 5220 to the measurement unit 5200, then a brainwave feature is created at the feature extraction unit 5500 and transmitted to the pleasantness/unpleasantness determination unit 5600, and the degree of unpleasantness of unknown stimulation or environment is differentiated/estimated using the degree of unpleasantness determination value. The degree of unpleasantness is (optionally) made visible at the differentiation level visualization unit 5800. Such a series of processes can be materialized by a computer or mobile terminal comprising a processor and a memory, or a dedicated electrical circuit. A dedicated electrical circuit can be a single integrated circuit or a plurality of electrical circuits. The processes can also be materialized by a software or by controlling a required hardware.

(Psychological Stress Feature)

In one aspect, the present invention provides a method of determining pleasantness/unpleasantness with a negative level for a waveform during latency compared to a standard waveform.

In one embodiment, the negative level is dependent on the environment or stimulation processed by an object, but it can advantageous if it is based on a waveform in a range after 150 milliseconds from stimulation, preferably is based on a waveform in a range after 300 milliseconds from stimulation, a waveform in a range of 300 milliseconds to 800 milliseconds after stimulation, or a waveform in a range of 300 milliseconds to 600 milliseconds after stimulation, and preferably is based on a (negative) occupancy in a range of 300 milliseconds to 800 milliseconds after stimulation. In addition to or in place of the occupancy, features including the mean amplitude of a specific time range, integrated value of amplitude, peak amplitude, peak latency, persistent time of effect, and frequency power can be used.

Psychological stress can be determined using the pleasantness/unpleasantness determination device defined by the negative level.

Other Embodiments

The pain estimation apparatus according to one or more embodiments of the invention has been described based on the embodiments, but the present invention is not limited to such embodiments. Various modifications applied to the present embodiments and embodiments constructed by combining constituent elements in different embodiments that are conceivable to those skilled in the art are also encompassed within the scope of one or more embodiments of the invention as long as such embodiments do not deviate from the intent of the inventions.

For example, a peak to peak value can be used as the amplitude value of brainwave data in each of the embodiments described above, but the amplitude value is not limited thereto. For example, a simple peak value can be used as the amplitude value.

In the embodiment described above, the range of the value of magnitude of degree of unpleasantness is set so that the value of Pmax, which is the magnitude of degree of unpleasantness corresponding to the upper limit value Amax of a brainwave amplitude, would be 1, or the value of Pmin, which is the magnitude of pain corresponding to the lower limit value Amin of the brainwave amplitude, would be 0, but this is not a limiting example. For example, the magnitude of the degree of unpleasantness can be represented by 0 to 100. In such a case, the pleasantness/unpleasantness determination unit 5600 can estimate the value Px of magnitude of degree of unpleasantness by the following equation.

$$Px = P\max \times (Ax - A\min)/(A\max - A\min)$$

Curve fitting was described above as an example of generating a pleasantness/unpleasantness determination value by analyzing a plurality of brainwave data, but this is not a limiting example. A predetermined value can also be used as the upper limit value of a brainwave amplitude. The predetermined values is for example 50 μV to 100 μV, which can be experimentally or empirically determined. In such normal analysis, data from about plus or minus 50 μV to 100 μV is eliminated as an artifact removal method. Such artifact removal can also be performed in the present invention as needed.

If the magnitude of the degree of unpleasantness felt by an object 5099 changes depending on the stimulation type or application environment, stimulation applied to the object 5099 by the stimulation application unit 5920 (see FIG. 17) can be any type of stimulation. However, when determining a degree of unpleasantness separated from physical intensity of stimulation, it is particularly desirable to apply the same stimulation or stimulation that is similar as much as possible under different environments or conditions. This is referred to as "context dependent degree of unpleasantness detection method" or "context dependent reference testing methodology". For example, the methods include, as shown in Examples of the invention, 1) a methodology of applying the same high temperature stimulation (e.g., 40° C.) in different stimulation application contexts (38° C. context or 48° C. context) to detect different degrees of unpleasantness, 2) method of performing the same cognitive processing under different circumstances (e.g., with or without monitoring) to detect latent degree of unpleasantness, and the like.

Some or all of the constituent elements of the pleasantness/unpleasantness determination apparatus in each of the embodiments described above can be comprised of a single system LSI (Large Scale Integration). For example, as shown in FIG. 17, the pleasantness/unpleasantness determination apparatus 5300 can be comprised of a system LSI having optionally the measurement unit 5200 and optionally the stimulation application unit 5920.

System LSI is ultra-multifunctional LSI manufactured by integrating a plurality of constituents on a single chip, or specifically a computer system comprised of a microprocessor, ROM (Read Only Memory), RAM (Random Access Memory), and the like. A computer program is stored in a ROM. The system LSI accomplishes its function by the microprocessor operating in accordance with the computer program.

The term system LSI is used herein, but the term IC, LSI, super LSI, and ultra LSI can also be used depending on the difference in the degree of integration. The methodology for forming an integrated circuit is not limited to LSI. An integrated circuit can be materialized with a dedicated circuit or universal processor. After the manufacture of LSI, a programmable FPGA (Field Programmable Gate Array) or reconfigurable processor which allows reconfiguration of the connection or setting of circuit cells inside the LSI can be utilized.

If a technology of integrated circuits that replaces LSI by advances in semiconductor technologies or other derivative technologies becomes available, functional blocks can obviously be integrated using such technologies. Application of biotechnology or the like is a possibility.

One embodiment of the invention can be not only such a pleasantness/unpleasantness determination value generation, pleasantness/unpleasantness determination apparatus, but also a pain classifier generation, pain differentiation/classification method using characteristic constituent units contained in a pain estimation apparatus as steps. Further, one embodiment of the invention can be a computer program implementing each characteristic step in pleasantness/unpleasantness determination value generation, pleasantness/unpleasantness determination methods on a computer. One embodiment of the invention can also be a computer readable non-transient recording medium on which such a computer program is recorded.

In each of the embodiments described above, each constituent element can be materialized by being configured with a dedicated hardware or by implementing software program that is suited to each constituent element. Each constituent element can be materialized by a program implementation unit, such as a CPU or a processor, reading out and implementing a software program recorded on a recording medium such as a hard disk or semiconductor memory. In this regard, software materializing the pain estimation apparatus of each of the embodiments described above or the like can be a program such as those described above herein.

As used herein, "or" is used when "at least one or more" of the listed matters in the sentence can be employed. When explicitly described herein as "within the range of two values", the range also includes the two values themselves.

Reference literatures such as scientific literatures, patents, and patent applications cited herein are incorporated herein by reference to the same extent that the entirety of each document is specifically described.

As described above, the present invention has been described while showing preferred embodiments to facilitate understanding. The present invention is described hereinafter based on Examples. The above descriptions and the following Examples are not provided to limit the present invention, but for the sole purpose of exemplification. Thus, the scope of the present invention is not limited to the embodiments or the Examples specifically described herein and is limited only by the scope of claims.

EXAMPLES

Examples are described hereinafter. The objects used in the following Examples were handled, as needed, in compliance with the standards set forth by the Osaka University, and the Declaration of Helsinki and ICH-GCP in relation to clinical studies.

Example 1: Differentiation of Stimulation Types with Different Degrees of Unpleasantness and the Similar Pain Intensities This Example performed differentiation of two types of pain stimulations with different degrees of unpleasantness by machine learning (SVM-RFE). As the two types of stimulations, pleasant electrical stimulation used in massage and low temperature stimulation with high degree of unpleasantness were used. The stimulation intensity thereof was regulated by subjective reporting.

(Method)
(Participants)

The same group of 41 healthy adult subjects in their 20s to 70s participated in low temperature stimulation paradigm and electrical stimulation paradigm experiments. Informed consent was obtained from the participants prior to the experiment. All participants self-reported as having no history of a neurological and/or psychiatric illness, or acute and/or chronic pain under clinical drug therapy conditions. This Example was in compliance with the Declaration of Helsinki and conducted under approval of the Osaka University Hospital ethics committee.

(Experimental Stimulation and Procedure)

Figure 1:
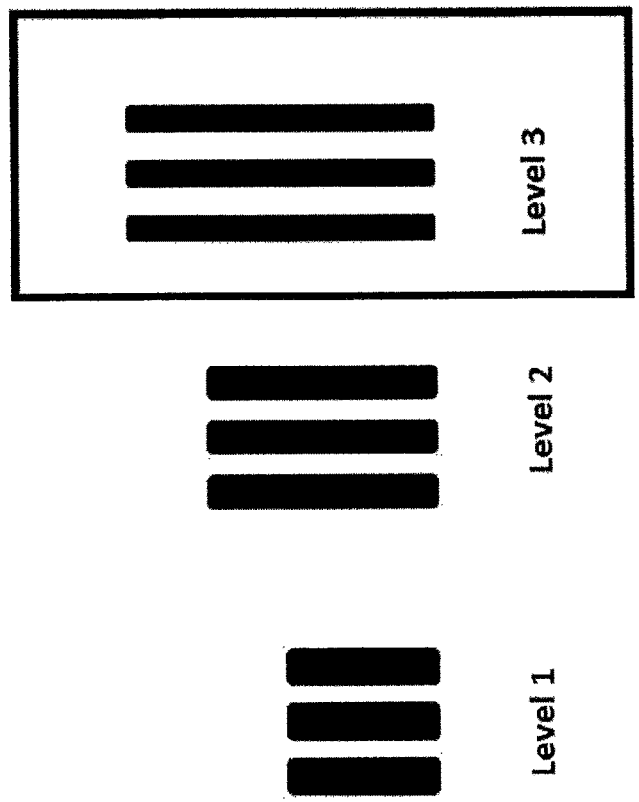
FIG. 1 shows an experimental paradigm for differentiating a difference in the degree of unpleasantness of pain due to different stimulation types. Low temperature stimulation (level 3) of −10° C. was used as unpleasant pain stimulation, and electrical stimulation (level 3) with an intensity level regulated for each individual was used as corresponding pleasant pain stimulation. Each level included three stimulations and lasted for 15 seconds.

The outline of the experimental method is illustrated in FIG. 1. A temperature stimulation system (Pathway; Medoc Co., Ltd., Ramat Yishai, Israel) was used to apply low temperature stimulation to the right forearm of the participants. The low temperature stimulation included three levels of temperature intensities (10° C., 0° C., and −10° C.) Each temperature level consisted of three stimulations with a 20 second inter-stimulus interval (ISI). Each stimulation had a plateau lasting for 5 seconds, and the waiting period for increase and decrease from the standard temperature (35° C.) was about 10 seconds. After three stimulations at each level, the intervals between blocks lasted 100 seconds. The participants continuously evaluated pain intensities in the range of 0 to 100 (0: "no pain"; 100: "unbearable pain") on a computerized visual analog scale (COVAS). COVAS data was simultaneously recorded with changes in stimulation intensities. In the electrical stimulation paradigm, electrical stimulation intensities corresponding to low temperature stimulations 10° C., 0° C., and −10° C. were first identified using a quantitative perception and pain sensation analyzer (PAINVISION CO., Ltd., Osaka, Japan) for each individual. Three stimulations each of three levels of electrical stimulation (weak, moderate, and strong) were applied by the same application method as the low temperature stimulation. Participants subjectively evaluated pain levels using COVAS in parallel with the application of stimulation.

(EEG Analysis)
(Extraction of Feature of Amplitude)

The following regression filter was applied to the continuously EEG data under low temperature and electrical stimulation conditions to remove eye movement noise (EOG).

Raw $EEG = \beta \times EOG + C$ $$EEG \text{ estimate} = \text{raw } EEG - \beta \times EOG \quad \text{[Numeral 1]}$$

μ: regression coefficient
C: intercept
EEG estimate: estimated EEG

Since Fp1 data is the closest to the left eye and heavily affected by eye movement, Fp1 data was used as EOG data. After EOG correction, epoch waveforms from 5 seconds before applying stimulation to 15 seconds after applying stimulation were sampled for each stimulation at each level. After baseline correction using the mean potential before applying stimulation, artifacts were removed at ±100 μV. The potential was converted to absolute values, and then standardized with the maximum amplitude, and mean amplitude for 15 seconds after applying stimulation was found for each level as the amplitude features (four features: Fz, Cz, C3, and C4). As the feature of pleasantness/unpleasantness, only intensity level 3 subjectively reported as definitely "painful" was used for both low temperature stimulation and electrical stimulation.

(Extraction of Feature of Frequency Power)

For frequency analysis, EOG correction processing was applied to the entire EEG data and then brainwave data from the start of stimulation to 15 seconds after applying stimulation was sampled for each stimulation level. After Fourier transform was applied, the frequency power was calculated (data for log 10 conversion of real number portion). The mean value of power was calculated for each level for each of δ (1 to 3 Hz), A (4 to 7 Hz), α (8 to 13 Hz), β (14 to 30 Hz), and γ (31 to 100 Hz) and standardized with the maximum value for each individual using data for all levels as the frequency feature (20 features: 4 electrodes×5 bands). As the feature of pleasantness/unpleasantness, only intensity level 3 subjectively reported as definitely "painful" was used for both low temperature stimulation and electrical stimulation.

(Pleasantness/Unpleasantness Differentiation Analysis)

Figure 2:
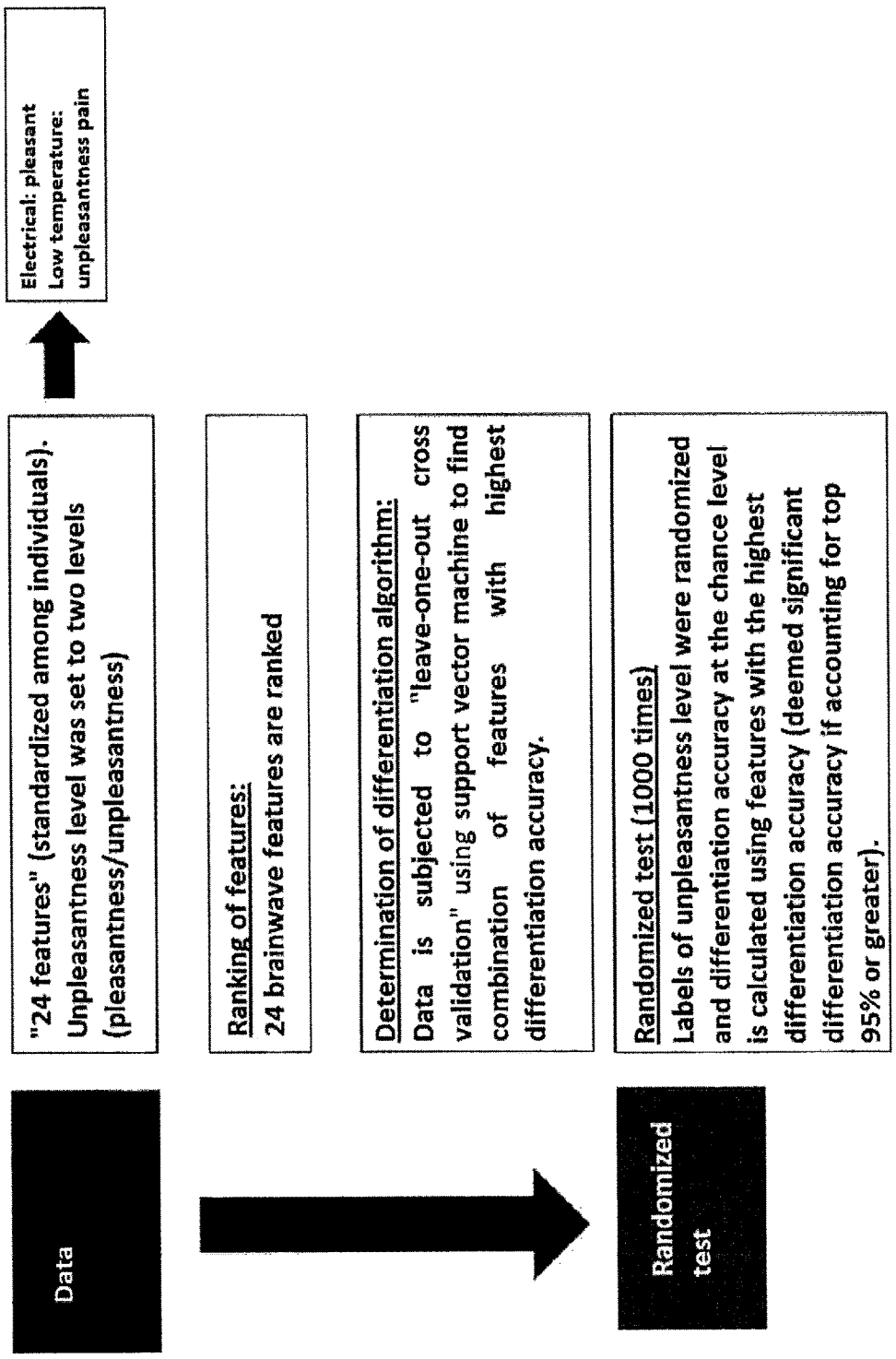
FIG. 2 shows a process of differentiation analysis on unpleasant pain. Differentiation analysis was performed using support vector machine. More specifically, SVM-RFE (Support vector machine recursive feature elimination) was used. First, 24 brainwave features were ranked. Differentiation accuracy was studied by leave-one-out cross validation while increasing features one at a time from top of the ranking. Lastly, differentiation accuracy at a chance level was studied by a randomized test using a group of features with the highest differentiation accuracy.
Figure 3:
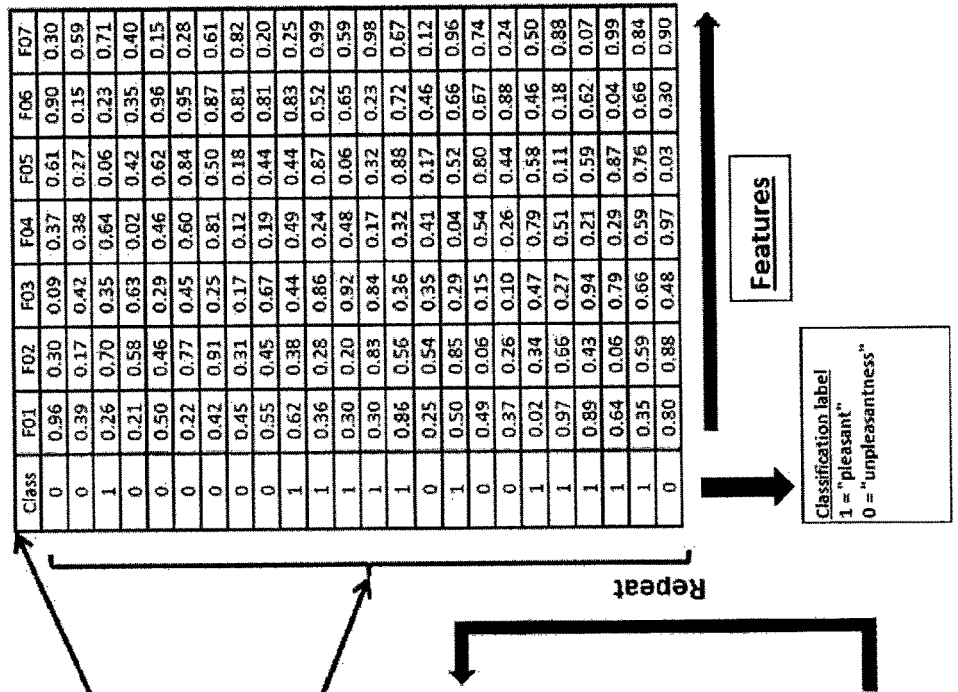
FIG. 3 shows a general process of SVM-RFE (A) and a more detailed internal process (B).

Unpleasantness stimulation (low temperature stimulation) and pleasant stimulation (electrical stimulation) on 41 participants were differentiated using Support Vector Machine Recursive Feature Elimination (SVM-RFE) (Guyon I, Weston J, Barnhill S, & Vapnik V. Gene selection for cancer classification using Support Vector Machine. Machine Learning 46, 389-422, 2002) (FIG. 2). As shown in FIG. 2, "24" features (standardized among individuals) were used. The unpleasantness level was set to "two levels (pleasantness/unpleasantness)". 24 brainwave features were ranked as the ranking of features. The differentiation algorithm was determined by finding a combination of features with the highest differentiation accuracy with "leave-one-out cross validation" of data using support vector machine (SVM). Randomized tests (1000 times) were conducted by randomizing the degree of unpleasantness labels and calculating differentiation accuracy for the chance levels using the number of features with the highest differentiation accuracy (deemed significant differentiation accuracy if accounting for the top 95% or greater). Statistical software package R and R-code of SVM-RFE (http://github.com/johncolby/SVM-RFE) were used for data analysis. As shown in FIG. 3, the rough flow of SVM-RFE comprises the process of repeating 1) training a differentiation instrument using training data, 2) ranking features, and 3) eliminating the feature with the lowest contribution, until the last feature is eliminated. The detailed flow is shown in FIG. 3B, which is specified as follows.

Terms
a) Training data: Sample=[$x_1$, $x_2$, ..., $x_k$, ..., x]
b) Classification label: Class=[1, 0, 1, 0, ..., $y_k$, ..., y]
c) Set of features remaining after RFE: Sfeature=[1, 2, ..., n]
d) Feature ranking: Rank=[ ]
Procedure
*Limit training data to remaining features: X=Sample (:, Sfeature)
*Train a differentiation instrument (SVM): Classifier=SVM (X, Class)
*Calculate weighting coefficients of feature: Weight=$\Sigma a_k y_k x_k$
*Calculate ranking criterion for all features: Criterion$_i$=(Weight$_i$)$^2$, for all $i$
*Find the feature with the lowest ranking criterion: F=argmain(Criterion)
*Update ranking list of remaining features: Rank=[Sfeature (F), Rank]
*Exclude feature with the lowest ranking criterion: Sfeature=Sfeature(1:f−1, f+1:length(Sfeature))
*Output feature ranking list: Feature ranked list r, This Example used 82 samples of 41 pleasant labels and 41 unpleasantness labels and 24 features for differentiation analysis. A radial basis (Gaussian) function was used as the kernel. The data was normalized.

$$\text{Radial basis function}: G(x1,x2)=\exp(-|x1-x2|^2) \quad \text{[Numeral 2]}$$

G: Gaussian function
x: data point
exp: exponential function.

(Results and Discussion)

Figure 5:
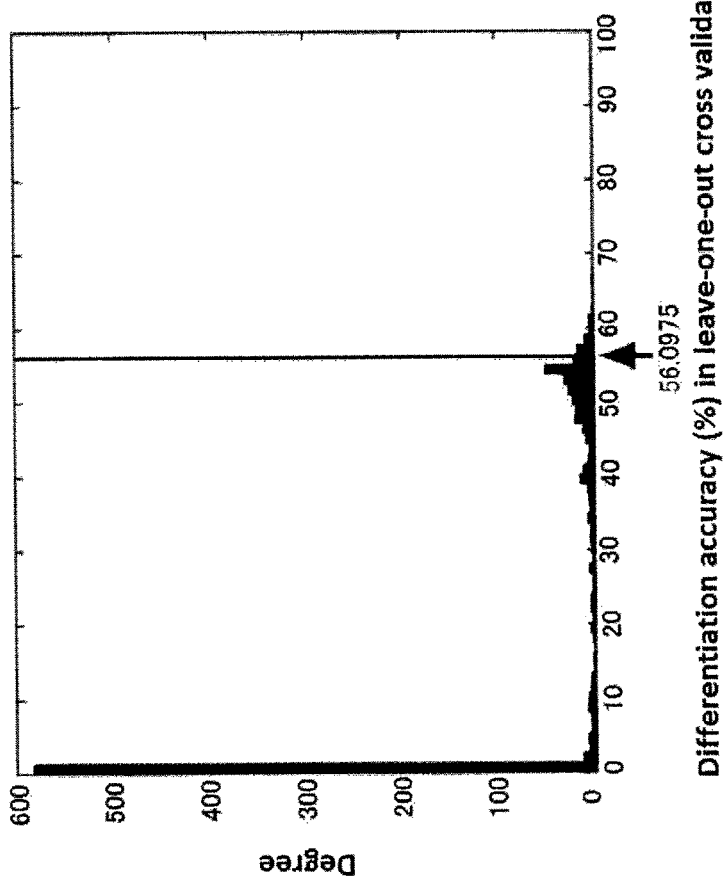
FIG. 5 shows results of a randomized test according to differentiation analysis of SVM using the top five ranking features. Differentiation labels were randomized 1000 times. Each time, the differentiation property was collected by leave-one-out cross validation. The actual differentiation accuracy of "56.098%" was at or within top 5% of a random distribution, indicating that significant differentiation accuracy is materialized.

FIG. 4 shows the ranking list of 24 features and pleasantness/unpleasantness differentiation accuracy of 82 samples when features were increased one at a time from top ranking features in order. Amplitude and frequency features at electrodes near the central portion of the scalp accounted for 80% of the top 10 features, which were, from the top, Cz(amplitude), C3(α), Cz(β), Fz(δ), Cz(γ), C4(β), C3(δ), Cz(α), Fz(α), and C3(θ). A differentiation instrument with the highest differentiation accuracy used the top five ranking features Cz(amplitude), C3(α), Cz(β), Fz(δ), and Cz(γ) and had differentiation accuracy of "56.098%". To confirm that this differentiation accuracy is not at a chance level but statistically significant, pleasantness/unpleasantness differentiation labels were randomized 1000 times to perform training using the top five characteristics. FIG. 5 shows a randomized distribution of differentiation accuracy. The actual differentiation accuracy of "56.098%" was within the top 95% of the random distribution, indicating that the accuracy is statistically significant.

The above results suggest that it is meaningful to create a differentiation instrument using a brainwave feature to differentiate stimulation types with different pleasantness/unpleasantness, and accuracy of the differentiation instrument has further room for improvement by finding and inputting features with high contribution.

Example 2: Differentiation of Same High Temperature Stimulations with Different Degrees of Unpleasantness This Example analyzed pleasantness/unpleasantness with high temperature pain stimulation. In particular, pleasantness/unpleasantness evaluation for the same high temperature stimulation was changed by changing the context of stimulation application, and pleasantness/unpleasantness was differentiated using an associated brainwave feature and a sigmoid function. This will demonstrate that it is possible to determine pleasantness/unpleasantness from controlled stimulation intensity for pain, which was difficult with simple conventional data association.

(Method)
(Participants)

25 healthy adult subjects in their 20s to 30s participated in a pain experiment using high temperature stimulation on two different dates. Informed consent was obtained from the participants prior to the experiment. All participants self-reported as having no history of a neurological and/or psychiatric illness, or acute and/or chronic pain under clinical drug therapy conditions. This Example was in compliance with the Declaration of Helsinki and conducted under approval of the Osaka University Hospital ethics committee.

(Procedure)

A temperature stimulation system (Pathway; Medoc Co., Ltd., Ramat Yishai, Israel) was used to apply high temperature stimulation to the right forearm of the participants. Two stimulation application conditions were used. Condition 1 was a weak pain context condition including 36° C. (base temperature), 40° C., and 38° C. There was a one minute 36° C. base segment at the beginning, and 40° C. and 38° C. stimulation segments randomly occurred three times each. In the 40° C. and 38° C. stimulation segments, 15 seconds of stimulation (5 seconds of leading edge and trailing edge) were continuously applied 5 times. The strong pain context condition included 36° C. (base temperature), 40° C., and 48° C. The stimulation application context was changed by replacing the 38° C. stimulation block with a 48° C. block. There was a one minute 36° C. base segment at the beginning, and 40° C. and 48° C. stimulation segments randomly occurred three times each, in the same manner for the weak pain context condition. In the 40° C. and 48° C. stimulation segments, 15 seconds of stimulation (5 seconds of leading edge and trailing edge) were continuously applied 5 times. The participants continuously evaluated pain intensities in the range of 0 to 100 (0: "no pain"; 100: "unbearable pain") on a computerized visual analog scale (COVAS). COVAS data was simultaneously recorded with changes in stimulation intensities.

(EEG Data Record)

Commercially available Bio-Amplifier (EEG 1200: Nihon Koden) was used to record EEG from seven scalp Ag/AgCl electrodes (Fp1, Fp2, F3, F4, C3, C4, and Pz). The frontmost electrodes Fp1 and Fp2 were used for eyeball potential (EGG) correction. Reference electrodes for guiding brainwaves were attached to both earlobes, and an earth electrode was placed on the center portion of the forehead. The sampling rate was 1000 Hz and amplified in the frequency band of 0.3 to 120 Hz. The impedance of all electrodes was less than 15 kΩ.

(EEG Analysis)

Continuous EEG data was sampled. To reduce EOG noise, the following regression filter was applied to raw EEG data:

Raw $EEG=\beta \times (Fp1+Fp2)+C$ $EEG$ estimate=raw $EEG-\beta \times (Fp1+Fp2)$ [Numeral 3]

β: regression coefficient
C: intercept
EEG estimate: estimated EEG

Fp1 and Fp2 data were added and used for amplifying the potential of vertical eye ball movement or blinking activity. After VEOG correction, a notch filter was applied to all EEG data to remove ham noise (60 Hz). Brainwave data for 15 seconds from start of stimulation was extracted for each stimulation of 36° C. (weak and strong pain context: 1 epoch), 40° C. (weak and strong pain context: 5 epochs×2 blocks), 38° C. (weak pain context: 5 epochs×2 blocks), and 48° C. (strong pain context: 5 epochs×2 blocks). After converting the amplitudes to absolute values, potential exceeding 100 μV was subjected to artifact removal and standardized using the maximum amplitude. The mean value of amplitudes (absolute value, and standardized) was found in the time direction for each stimulation, and the overall mean amplitude was found for each temperature stimulation.

(Analysis of Subjective Evaluation)

In the same manner for brainwave data, data was extracted for each stimulation of 36° C. (weak and strong pain context: 1 epoch), 40° C. (weak and strong pain context: 5 epochs×2 blocks), 38° C. (weak pain context: 5 epochs×2 blocks), and 48° C. (strong pain context: 5 epochs×2 blocks). Since subjective evaluation is delayed and changes after application of pain stimulation, the extracted time frame was from 10 seconds after application of stimulation to the next application of stimulation. The maximum value in this segment was used as the evaluation point, and the overall mean point was calculated under each temperature condition.

(Statistical Analysis)

Before the statistical test, numerical values of other temperature conditions were subjected to baseline correction based on the 36° C. brainwave amplitude and subjective evaluation score in order to align the comparative baseline for the weak pain context and strong pain context. To find the contextual effect of subjective evaluation, evaluation scores for the same temperature intensity, i.e., 40° C. condition, were compared using t-test between weak and strong contexts. Likewise for the brainwave amplitude, the mean value was found for F3 and F4, and the mean amplitudes under the 40° C. condition were compared using a t-test between weak and strong contexts.

(Differentiation Model)

After creating a degree of unpleasantness differentiation instrument using a brainwave amplitude by sigmoid function fitting, a numerical value of an inflection point was calculated as a degree of unpleasantness determination value. 40° C. stimulation in a different context was differentiated based on the determination value.

(Results)

Figure 6:
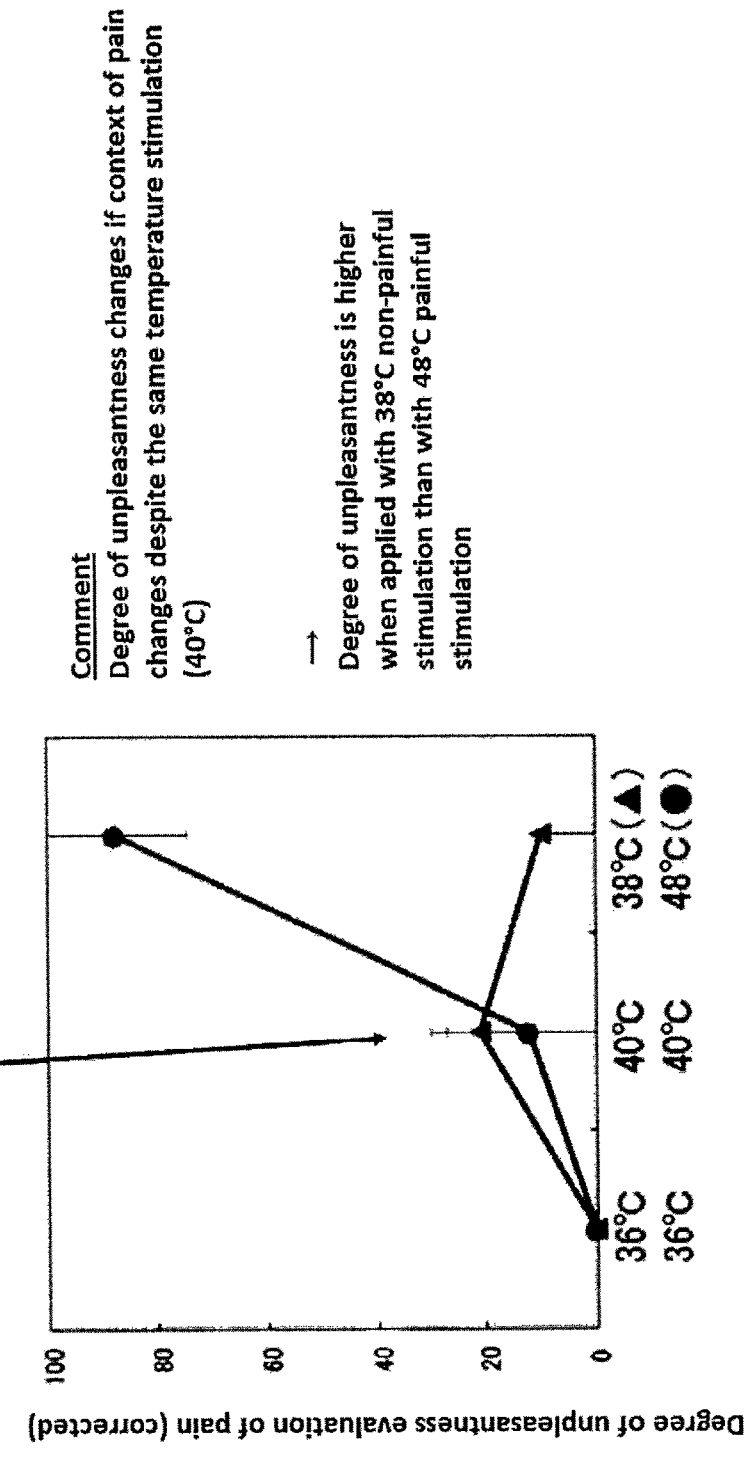
FIG. 6 shows a pain context effect (subjective evaluation) of the same high temperature stimulation. It was demonstrated that the degree of unpleasantness (subjective evaluation) changes if the context (environment) of pain changes, despite of the same temperature stimulation (40° C.) Specifically, it was demonstrated that the degree of unpleasantness of stimulation at 40° C. is higher when applied together with "not painful" stimulation of 38° C. than when applied together with "painful" stimulation of 48° C.

FIG. 6 shows results of subjective evaluation. The degree of subjective evaluation was significantly different for the same 40° C. stimulation in a 38° C. weak pain context and 48° C. strong pain context when the common baseline was 36° C. Specifically, it was observed that a higher degree of unpleasantness was felt from 40° C. stimulation when applied in the same application context as 38° C. weak pain stimulation compared to a 48° C. strong pain context.

Figure 7:
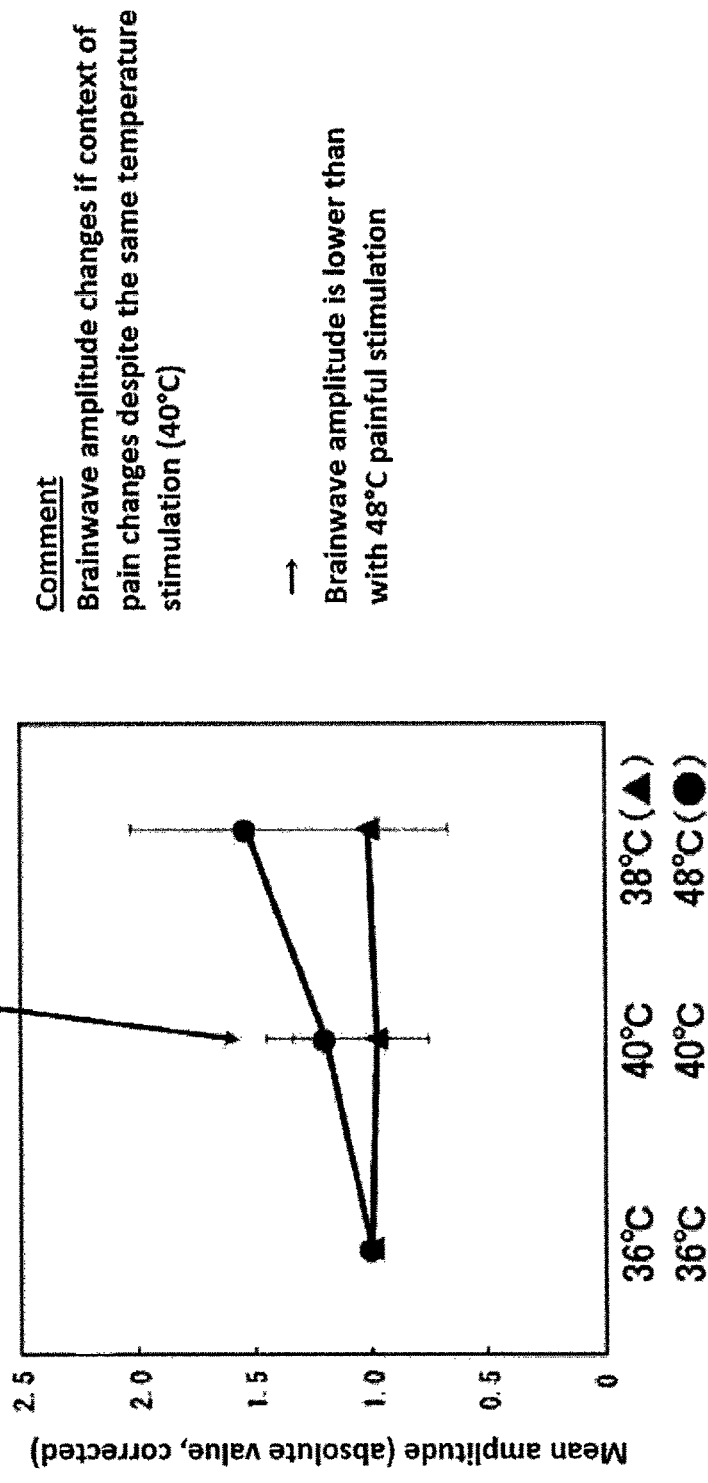
FIG. 7 shows a pain context effect (brainwave amplitude) of the same high temperature stimulation. It was demonstrated that the brainwave amplitude changes if the context (environment) of pain changes, despite of the same temperature stimulation (40° C.). The brainwave amplitude would be lower when applied together with painful stimulation of 48° C.

There was also a significant difference in the brainwave amplitude in response to 40° C. stimulation from a frontal electrode between weak and strong contexts. A higher amplitude was exhibited for the strong context (FIG. 7). This suggests that high brain activity under the 48° C. condition elicits high activity under the 40° C. condition by a context effect, and the high activity affects the evaluation standard to relatively reduce subjective evaluation.

Figure 8:
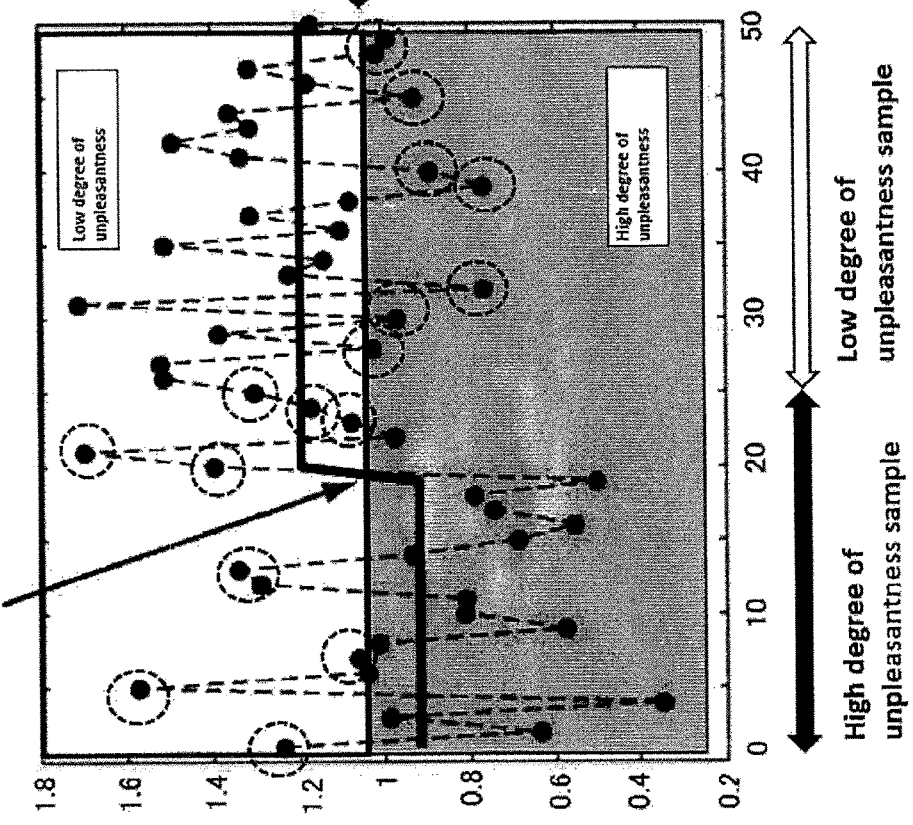
FIG. 8 shows an unpleasant pain differentiation instrument (sigmoid function). Pain with different degrees of unpleasantness is separated by using a threshold value of an inflection point. Pain is determined to have a low degree of unpleasantness if >1.0555, and determined to have a high degree of unpleasantness if 1.0555. The overall differentiation accuracy was 64%. The breakdown thereof was 68% for differentiation accuracy of low degree of unpleasantness and 60% for differentiation accuracy of high degree of unpleasantness.

FIG. 8 shows results of differentiation analysis on 25 samples for unpleasant stimulation and 25 samples for pleasant stimulation using a sigmoid function. The following differentiation instrument (sigmoid function) was obtained by fitting.

$$y=0.92+0.2774/(1+10^{(19.67-x)\times 88.12})$$ [Numeral 4]

A threshold value of an inflection point was "1.0555". A sample was differentiated as "low degree of unpleasantness" when a feature was higher than the threshold value, and "high degree of unpleasantness" when lower than the threshold value. When all 50 samples were differentiated based on this differentiation standard, the overall error rate was "36%", resulting in differentiation accuracy within the range of 60 to 70%. A difference in the degree of unpleasantness associated with the stimulation of the same physical amount exhibiting a differentiation result exceeding the chance level with a simple binomial differentiation function is a notable result of the present invention. A more strict unpleasant pain evaluation can be materialized by a context dependent reference testing methodology that applies stimulation with the same physical amount in difference application contexts. In this manner, it was demonstrated that degree of unpleasantness evaluation can accurately judge the actual degree of unpleasantness of a subject that cannot be read out from a brainwave amplitude.

Figure 9:
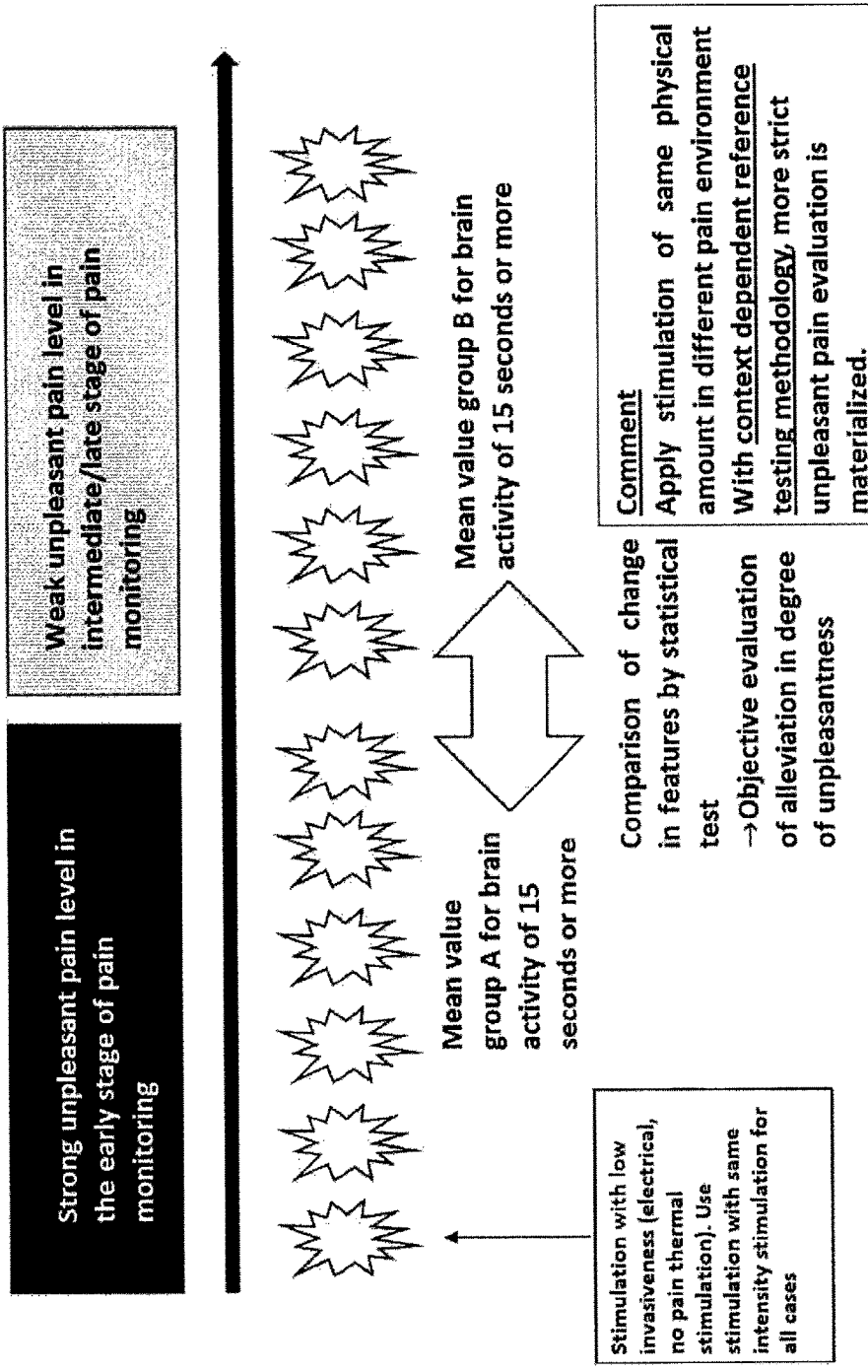
FIG. 9 shows an application example of an unpleasantness pain differentiation instrument (sigmoid function). The first half indicates that the strong unpleasant pain level in the early stages of pain monitoring is maintained, and the latter half indicates the weak unpleasantness pain level of the intermediate and late stages of pain monitoring. Groups (A and B) of mean values for brain activity of 15 seconds or more are obtained, and the change in features is compared by statistical tests to objectively evaluate the alleviation in the degree of unpleasantness. More strict unpleasant pain evaluation is materialized by applying the same physical amount of stimulation under different pain environments with "context dependent reference testing methodology".

FIG. 9 shows an application example of this Example. When persistent unpleasant pain is monitored and alleviated in a clinical setting, a strong degree of unpleasantness condition is expected to gradually transition to a weak degree of unpleasantness condition as shown in the figure. The degree of unpleasantness differentiation instrument in the invention uses the following process to differentiate/estimate the change in the degree of unpleasantness.
1. Stimulation with low invasiveness (electrical or thermal stimulation) is applied to a patient in the background at a constant intensity and interval. 2. A mean amplitude (absolute value; standardized with amplitude of first stimulation or the like) for-a certain time frame (e.g., 15 seconds) is continuously calculated in accordance with temporal changes, and the trend thereof is displayed. 3. A plurality of mean amplitudes are separated into front and back groups in terms of time (10 amplitudes for each group or the like) and compared by a t-test to find a significant point of pattern change.

Since such an objective evaluation method of change in unknown unpleasant pain levels is a methodology using a stimulation application context, the method can be referred to as a "context dependent reference testing methodology".

Example 3: Differentiation of Latent Stress During Cognitive Tasks in Different Contexts In this Example, a cognitive competitive task (Stroop task) experiment was conducted by setting different task performance contexts as a psychological stress paradigm.

(Method)
(Participants)

26 healthy adult subjects in their 20s to 30s participated in a Stroop task experiment on two different dates. Informed consent was obtained from the participants prior to the experiment. All participants self-reported as having no history of a neurological and/or psychiatric illness, or acute and/or chronic pain under clinical drug therapy conditions. This Example was in compliance with the Declaration of Helsinki and conducted under approval of the Osaka University Hospital ethics committee.

(Method)

Figure 10:
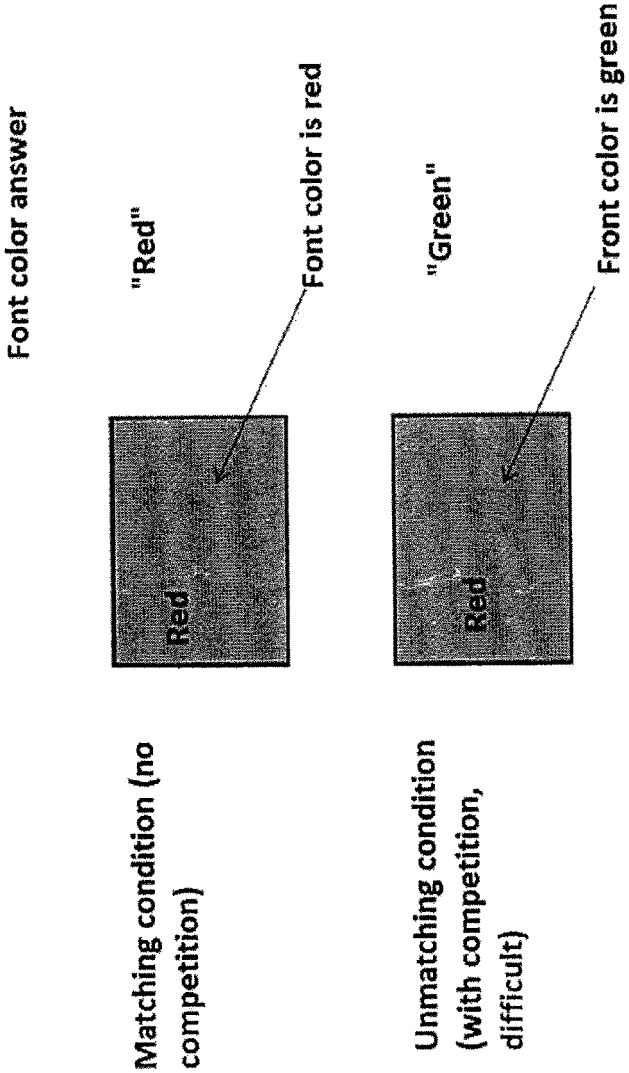
FIG. 10 is an experiment of a psychological stress paradigm. A Stroop color task (cognitive competence task) is assigned as the cognitive task. Three blocks (50 runs each) of the font color task, i.e., answering the "font color", are performed. The upper side of FIG. 5 shows a scheme for conducting an experiment under a matching condition (no competition, font color matches the character information) and an unmatching condition (with competition, difficult, font color does not match the character information).

FIG. 10 shows an outline of the Stroop task performed. This Example used a "font color task" where participants answer the font color. Under a matching condition with low cognitive burden, the meaning of the characters (e.g., "red") and the font color were the same. Under an unmatching condition with a high cognitive burden resulting in competition during answering, the meaning of the characters and the font color were different. The task consisted of three blocks in total, and each block included 50 runs (25 runs for each condition). Subjects were asked to answer as quickly as possible. An error feedback was given by a ringing buzzer when an incorrect answer was given. Under a stress free condition, the experiment was performed alone, with no supervisor during the performance of task, and no experiment conductor within the field of vision. Under a stressful condition, an unknown male supervisor sat within 1 meter at the diagonally left side and monitored the participants silently throughout while wearing a mask.

(EEG Data Record)

Commercially available Bio-Amplifier (EEG 1200: Nihon Koden) was used to record EEG from seven scalp Ag/AgCl electrodes (Fp1, Fp2, F3, F4, C3, C4, and Pz). The frontmost electrodes Fp1 and Fp2 were used for EOG correction. Reference electrodes for guiding brainwaves were attached to both earlobes, and an earth electrode was placed on the center portion of the forehead. The sampling rate was 1000 Hz and amplified in the frequency band of 0.3 to 120 Hz. The impedance of all electrodes was less than 15 kU.

(EEG Analysis)

Continuous EEG data was sampled. To reduce EOG noise, the following regression filter was applied to raw EEG data:

Raw $EEG=\beta \times (Fp1+Fp2)+C$ $EEG$ estimate=raw $EEG-\beta \times (Fp1+Fp2)$ [Numeral 5]

$\beta$: regression coefficient
C: intercept
EEG estimate: estimated EEG

Fp1 and Fp2 data were added and used for amplifying the potential of vertical eye ball movement or blinking activity. After VEOG correction, a 0.3 Hz to 40 Hz band frequency filter was applied to remove low frequency and high frequency components. Brainwave data epochs from 200 milliseconds before presenting the characters to 800 milliseconds after the presentation was sampled for each condition (50 epochs×2 conditions×2 context conditions). Baseline correction was performed using the mean amplitude before application of stimulation. An epoch observed with an amplitude of ±50 μV was removed from subsequent analysis. The remaining epochs were averaged for each individual, and then standardized using the maximum amplitude absolute value for all data including two conditions (matching, unmatching) and all electrodes (F3, F4, C3, C4, and Pz).

(Differentiation Analysis)

A degree of unpleasantness differentiation instrument in a psychological stress context was created by sigmoid function fitting. Since a difference in context is notably manifested in the persistence of the negative potential effect as a feature as shown in the results, occupancy (total time for negative potential (or number of data points for negative potential)/overall time (or total number of data points)×100) of a negative effect in a specific time range was conceived and used. A numerical value of an inflection point in a fitting function was calculated as a degree of unpleasantness determination value. Based on the determination value, degree of stress, i.e., degree of unpleasantness, in different contexts was differentiated.

(Results)
(Behavioral Data)

Figure 11:
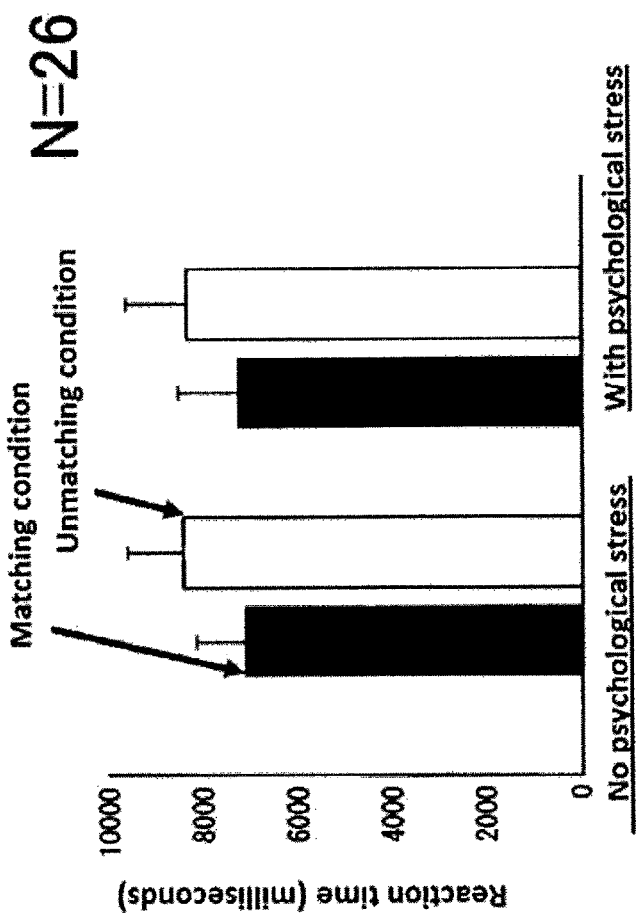
FIG. 11 shows behavioral data (reaction time required for answering) in a psychological stress paradigm. The left side is no psychological stress (no monitoring during the task by a third party), and the right side is with psychological stress (with monitoring by a third party). The response time is longer for the difficult unmatching condition. A significant difference was not found between any condition in the reaction time with or without psychological stress. Thus, it was concluded that an obvious effect of having stress or no stress was not found.

FIG. 11 shows comparative results of reaction time required for answering under matching or unmatching condition in a psychological stress free context and psychologically stressful context. In both contexts, the reaction time required for answering was longer under an unmatching condition compared to a matching condition, such that it was confirmed cognitive burden is high under an unmatching condition. Meanwhile, a significant difference was not found in the reaction times between contexts. A difference in manifested stress did not manifest in the reaction time. This is a result that is in alignment with the fact that hardly any difference in subjective report related to stress during the task of the participants was observed between contexts.

Figure 12:
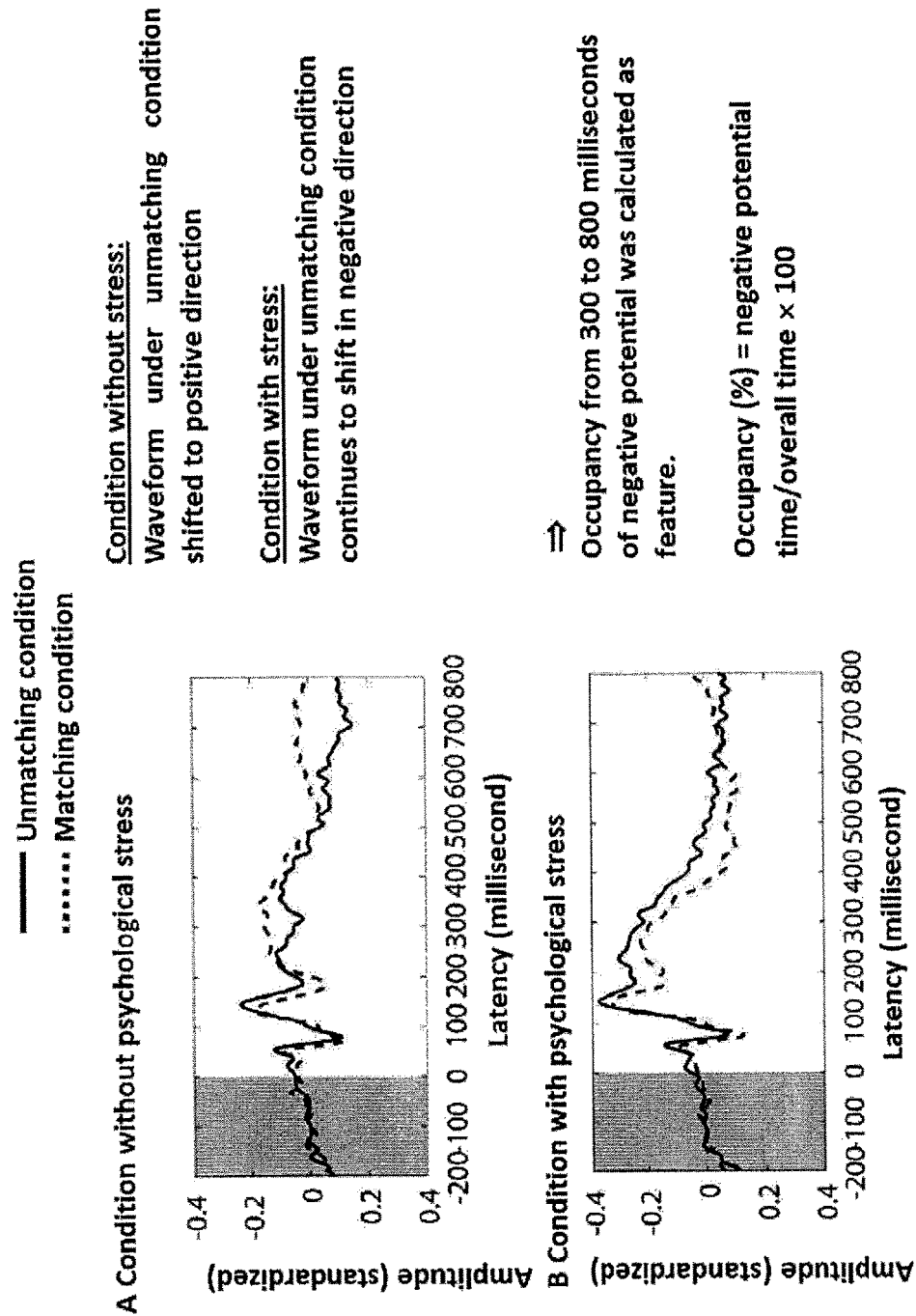
FIG. 12 shows a result for brainwave data (event-related potential: left frontal at F3). The solid line is for the unmatching condition, and the dotted line is for the matching condition (comparative standard condition). The top (A) shows a pleasant condition (no psychological stress), and the bottom (B) shows an unpleasant condition (having psychological stress). The waveform for the unmatching condition shifted to the positive direction under a pleasant condition (no psychological stress). The waveform for the unmatching condition continued to shift to the negative direction under the unpleasant condition (having psychological stress). As an example, the occupancy from 300 to 800 milliseconds of negative potential was calculated and used as a feature. Occupancy (%)=negative potential time/overall time×100.

However, a significant difference was found between contexts in a comparison of a matching condition and unmatching condition for event-related potential at the frontal portion in FIG. 12. In the stress free context without monitoring during the task performance, a waveform under the unmatching condition was observed to be shifted downward, i.e., positive potential direction (from around 300 milliseconds after application of stimulation), compared to a waveform under a matching condition. Meanwhile, under a stressful condition with monitoring, such a shift to the positive potential direction was not observed, but rather a shift in the negative direction was observed. The shift to the negative direction was persistent from 200 milliseconds after application of stimulation.

Figure 13:
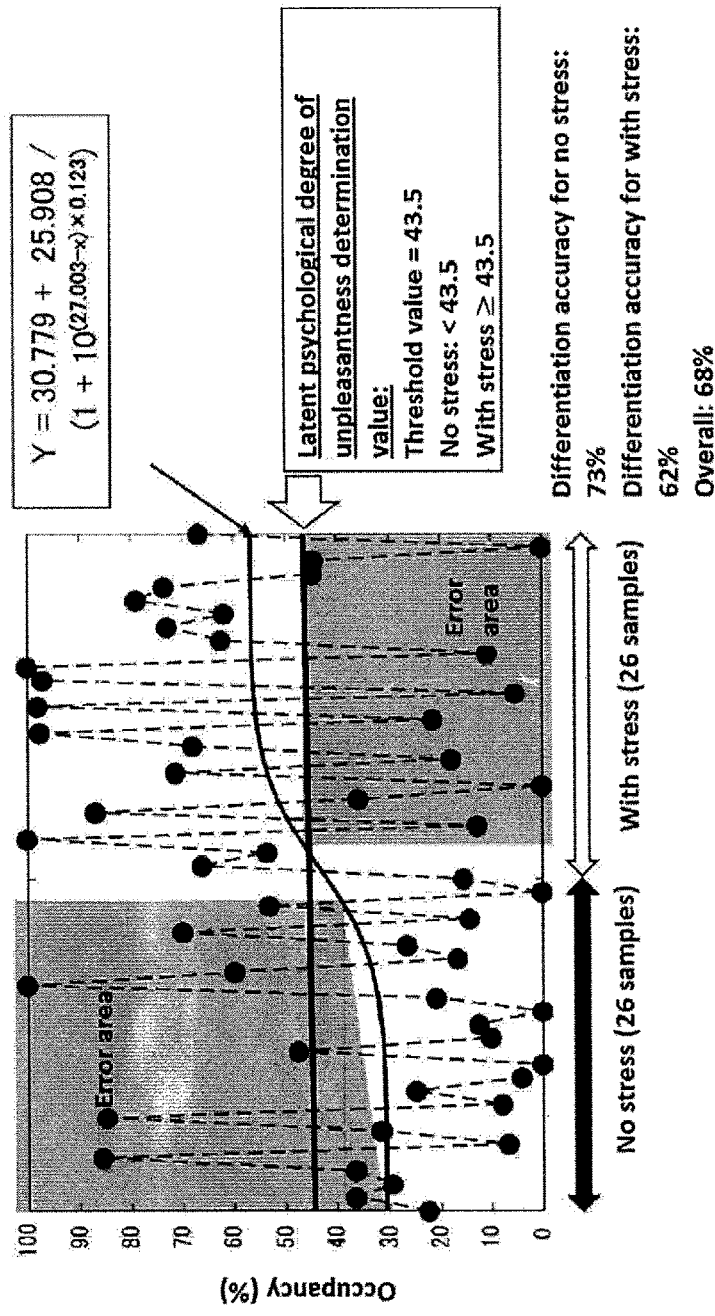
FIG. 13 is differentiation analysis (sigmoid function), showing a result of sigmoid fitting of the result in FIG. 12. A threshold value was found to be threshold value=43.5 as a latent psychological unpleasantness differentiation instrument. A value equal to or less than this value is determined as no stress, and a value exceeding this value is determined as having stress. The differentiation accuracy for no stress was 73.1%, and the differentiation accuracy for having stress was 61.5%. The overall differentiation accuracy was 67.6%.

The persistence of a negative potential effect is expressed as a feature of occupancy, and 26 samples for stress free conditions and 26 samples for stressful conditions were differentiated and analyzed (FIG. 13). As a differentiation instrument, a sigmoid approximation function was used, which is expressed by the following mathematical equation.

$Y=30.779+25.908/(1+10^{(27.003-X) \times 0.123})$ [Numeral 6]

The psychological degree of unpleasantness determination value according to an inflection point was "43.5". In particular, it is noteworthy that this degree of unpleasantness determination value is a threshold value for differentiating latent psychological degree of unpleasantness because the stress to be differentiated is not manifested in the answer time or subjective evaluation, but results in change in brain activity related to the frontal portion dominant suppression function. When 52 samples were differentiated with a value equal to or greater than a determination value of 43.5 as "stressful" and a value less than 43.5 as "stress free", the overall differentiation accuracy was "68%", exhibiting a numerical value that is about 20% higher than the chance level (50%).

Figure 14:
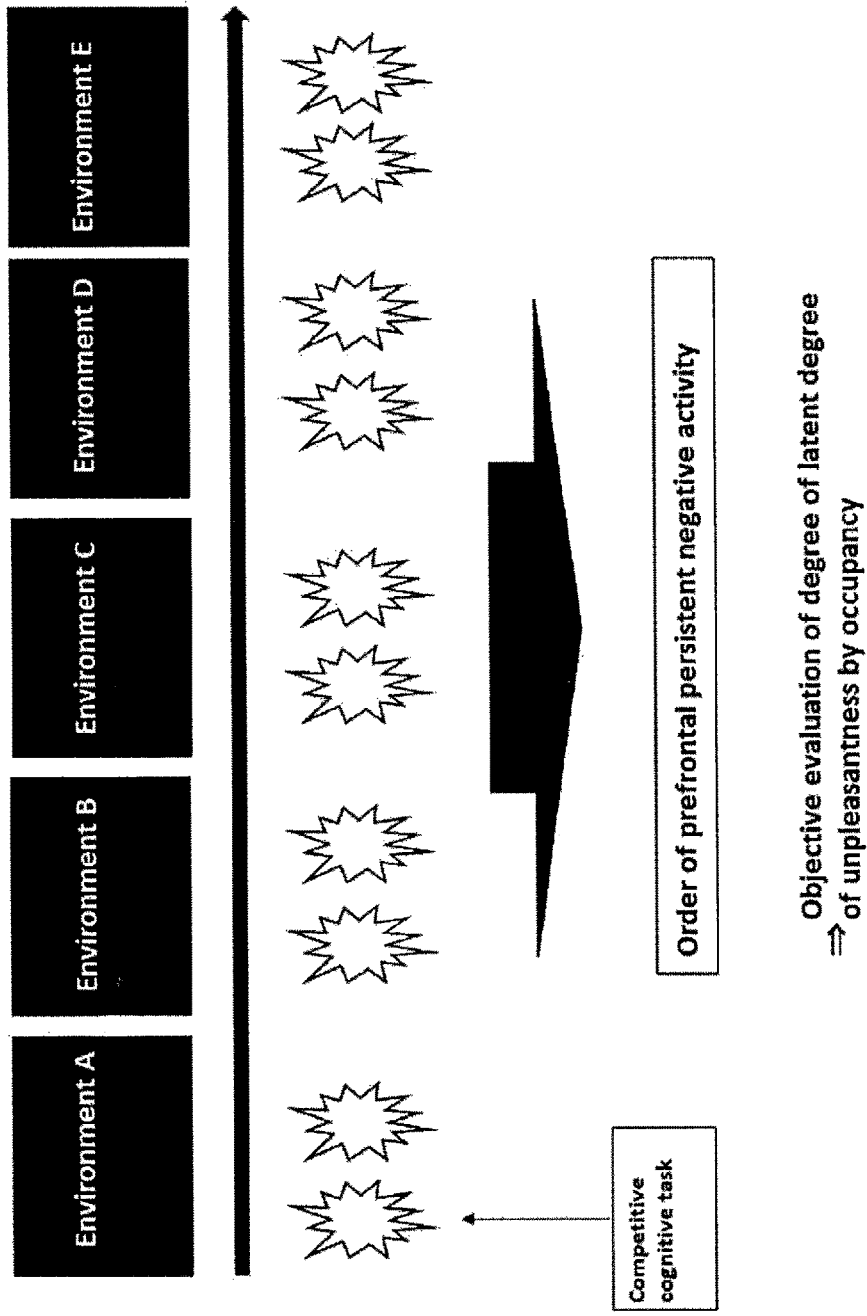
FIG. 14 shows an application example of a latent psychological degree of unpleasantness differentiation instrument (sigmoid function). The order of persistent negative activity in the prefrontal portion is studied. The latent degree of unpleasantness can be objectively evaluated with occupancy.

FIG. 14 shows an application example of this Example. At a workplace or educational environment, what kind of environment should be set up to mitigate latent stress that is hard to notice, or to elicit a suitable stress to increase work efficiency or improve motivation is an important issue. In this regard, as shown in the figure, a plurality of actual or simulated environmental conditions are prepared, a cognitive task used in this Example or the like is performed, and manifestation patterns of persistent negative potential activity are compared between conditions or ranked using an amplitude, frequency, or occupancy in the invention. An actual environment can be objectively set up at the workplace or educational setting by calculating the individual or population ranking. Industrial deployment thereof in applications such as environment evaluation or product evaluation can be expected.

(Example 4: Differentiation and Estimation of Pleasant/Unpleasant Pain Using an Individual Model: Utilization of Self-Replicated Feature by Sample Amplification Method)

(Method)
(Participants)

170 healthy adult subjects in their 20s to 70s participated in a high temperature paradigm experiment. Informed consent was obtained from the participants prior to the experiment. All participants self-reported as having no history of a neurological and/or psychiatric illness, or acute and/or chronic pain under clinical drug therapy conditions. This Example was in compliance with the Declaration of Helsinki and conducted under approval of the Osaka University Hospital ethics committee.

(Experimental Stimulation and Procedure)

A temperature stimulation system (Pathway; Medoc Co., Ltd., Ramat Yishai, Israel) was used to apply high temperature stimulation to the right forearm of the participants. High temperature stimulation included six levels of temperature intensities (increased by 2° C. from 40° C. to 50° C.). Each temperature level consisted of three stimulations and had a plateau lasting 5 seconds. The waiting period for increase and decrease from the standard temperature (35° C.) was about 10 seconds. After three stimulations at each level, the intervals between blocks lasted 100 seconds. The participants continuously evaluated pain intensities in the range of 0 to 100 (0="no pain"; 100="unbearable pain") on a computerized visual analog scale (COVAS). COVAS data was simultaneously recorded with changes in stimulation intensities.

(EEG Data Record)

Brainwaves were recorded continuously during the experiment from four electrodes at the frontal portions with an EEG system (Neurofax, Nihon Kohden). The lead electrodes were attached to the left and right earlobes, which were connected to the electrode on the scalp on the same side. An earth electrode was placed on the center portion of the forehead. The sampling frequency was 1000 Hz and amplified at 0.3 to 120 Hz. The impedance was maintained at or below 15 kΩ.

(EEG Analysis)
(Pre-Processing for Extraction of Feature of Amplitude)

The analysis procedure is shown in FIG. 19. Specific procedure is the following.

*Feature Extraction

1. Electrode extraction: Add a virtual EOG electrode (main component analysis) to four electrodes at Fp1, Fp2, F3, and F4.

2. Blinking (EOG) removal: Extraction of EOG component (first component) by main component analysis→apply a regression filter on the original data.

3. Reduction of myogenic potential (EMG): apply a 30 Hz high-cut filter.

4. Sample and "convert" brainwave from 5 seconds to 15 seconds after application of stimulation at level 1 (40° C.) and level 6 (50° C.) into absolute values (2×3 stimulations=6 epochs).

5. "Convert into z values" using a rest segment (for 30 seconds before application of stimulation).

*Amplification/Replication of Feature

1. Actually Measured Sample 1:
"Moving average" is multiplied while shifting a 5 second segment by 1 point each.
For each level, "30003 samples (10001 samples×3 stimulations)" are created.

2. Actually Measured Sample 2:
2.1 "30 samples" are created for each level without a point overlap in one second segments.
2.2 Normal random numbers or Pearson system random numbers are generated using a distribution property of an actually measured sample in each electrode, and a "self-replicated feature" for 10000 samples is amplified/created.

*A "sample amplification method" is a technique of dramatically increasing the sample size using the distribution property thereof when there are few samples.

*Differentiation Mode Creation and Evaluation

1. An individual differentiation model is created by machine learning (determination of coefficients by LASSO and Bayesian optimization)

2. Generalization capability of a model is confirmed by using another sample.

*Actual Differentiation Model Creation

EEG data for one participant (ID 185) was used for creating a differentiation model. An individual differentiation model can be created with all 170 subjects, but this Example created an individual model with only one subject to show how much a differentiation model created with only one subject can effectively function and can be generalized to other subjects. Eye movement noise (EOG) was first reduced. After main component analysis using data from four electrodes and extraction of a first component of EOG, a 0.5 to 30 Hz band pass filter was applied to emphasize and leave only an EOG component. An EOG component was then removed by using a regression filter. After removal of EOG, a 30 Hz high cut filter was applied to mitigate myogenic potential noise. Lastly, for "reverse utilization of noise", a virtual channel of EOG component obtained by main component analysis was added and amplified to five electrodes. An epoch from 5 seconds to 15 seconds after application of stimulation was sampled for three stimulations each with respect to level (40° C.) of "no pain" and level 6 (50° C.) of "unbearable unpleasant pain", and the amplitude was converted to an absolute value.

(Sample Amplification of Self-Replicated Feature)

Actual measured value samples for sample amplification were obtained from epoch data subjected to the noise processing described above by two methods, as shown in the procedure of FIG. 19. First, for each epoch, a moving average from shifting one point each was multiplied, using a 5 second segment unit, to obtain 10001 samples for each stimulation (30003 samples each for levels 1 and 6). Secondly, a method of obtaining a large replicated sample from a small actually measured sample in the truest sense was used to sample the same 10 second stimulation segment, by each second so as not to overlap, and a mean value for 10 samples was obtained. Two types of sample amplification methods were used on these samples. The first method is a method of generating "normal random numbers" using mean values and standard deviations of levels 1 and 6 (10000 times in this Example) to obtain "self-replicated feature" for 20000 samples. The second method is a method of generating "Pearson system random numbers" using distribution property values, i.e., mean value, standard deviation, kurtosis, and skew, to obtain an amplification feature. The background reasons for sample amplification methods are 1) observed data may not be ideal for model creation due to randomly generated noise or coarse distribution, and 2) there is often insufficient time to obtain a sufficient number (e.g., 1000 or 10000) of samples in actual pain monitoring. A technology of self-replicating a large volume of samples from few samples is one module of model creation technologies that is important for creating a differentiation model customized for individuals.

(Individual Differentiation Model Creation and Generalization Test)

As shown in FIG. 19, an individual differentiation model was created by machine learning from a sample of one subject by using the self-replicated feature described above, and no pain and unpleasant pain of the other 169 subjects were differentiated. FIG. 20 shows the specific method.

*Model Creation

1. By using 20000 replicated samples of an individual (ID 185) as learning data, a hyperparameter (λ) of a logistic regression model is determined by Lasso and Bayesian optimization, and weighting coefficients of features (five amplitudes) and a model intercept are determined.

*20000 samples amplified using normal random numbers and Pearson system random numbers are used.

*Model Evaluation

2. Test data for the other 169 subjects are differentiated and estimated using the determined individual model.

*Absolute mean amplitude (converted to z-value at rest) from 5 to 15 seconds after application of stimulation for brainwave data of the same experimental design was used as the test data (3 stimulations×2 levels×169 subjects).

3. The mean correct answer rate for 169 subjects is deemed the differentiation accuracy of the model.

*Actual Model Creation/Evaluation

Specifically, with 20000 amplified samples of one subject (ID 185) as learning data, a hyperparameter (λ) was determined using L1 regularization and Bayesian optimization, and five feature coefficients of a logistic regression model were determined. Other methods such as grid search can also be used for determining a hyperparameter. The difference therebetween is in a large difference in the methodology in that Bayesian optimization is a method of efficiently finding a macro solution (gain is the largest parameter setting in all region) while avoiding a bias toward a localized solution (e.g., vicinity of a parameter value in a specific region or a combination thereof) in a process of determining a hyperparameter performed when determining an objective function which is a differentiation model, whereas grid search comprehensively search all combinations (e.g., combination of Cost and γ in support vector machine) or the setting range (range of λ in this Example) and performs cross validation. The samples with no pain and unpleasant pain for the rest of 169 subjects were differentiated and estimated one at a time using the obtained individual differentiation model. As shown in FIG. 20, the overall mean amplitude from 5 seconds to 15 seconds after application of each stimulation at each level was calculated to reduce the noise level. Six samples (3 stimulations×2 levels) were used as test data per person. First, the result of using replicated samples amplified by the method of generating normal random numbers (use mean and SD) and Pearson system random number (use mean, SD, kurtosis, and skew) based on the distribution property of 20000 actually measured samples is shown. Next, a "sample amplification method from a small number to a large number" literally from 30 samples to 20000 samples is tested using a random number generation method with high differentiation accuracy to examine the possibility of pain differentiation and estimation using an individual differentiation model.

(Results and Discussion)

COVAS scores were calculated to find whether a subject (ID 185) whose individual differentiation model is created feels unpleasantness from the thermal stimulation used in the experiment. FIG. 21 is a result of calculating and plotting the maximum value during stimulation application time at each level and stimulation. From 40° C. to 44° C., the score was close to 0 and hardly any pain was felt, but the degree of unpleasantness of pain rapidly increased at 48° C. At 50° C. of level 6, the degree of unpleasantness finally reached the ceiling. In this regard, samples were amplified using actually measured samples of levels 1 and 6 in the creation of an individual differentiation model. The distribution of 30003 samples (3 stimulations×10001 samples) of each level is as shown in FIG. 22. It can be understood from visual inspection that the mean value and SD as well as the spread are greater for level 6.

Figure 23:
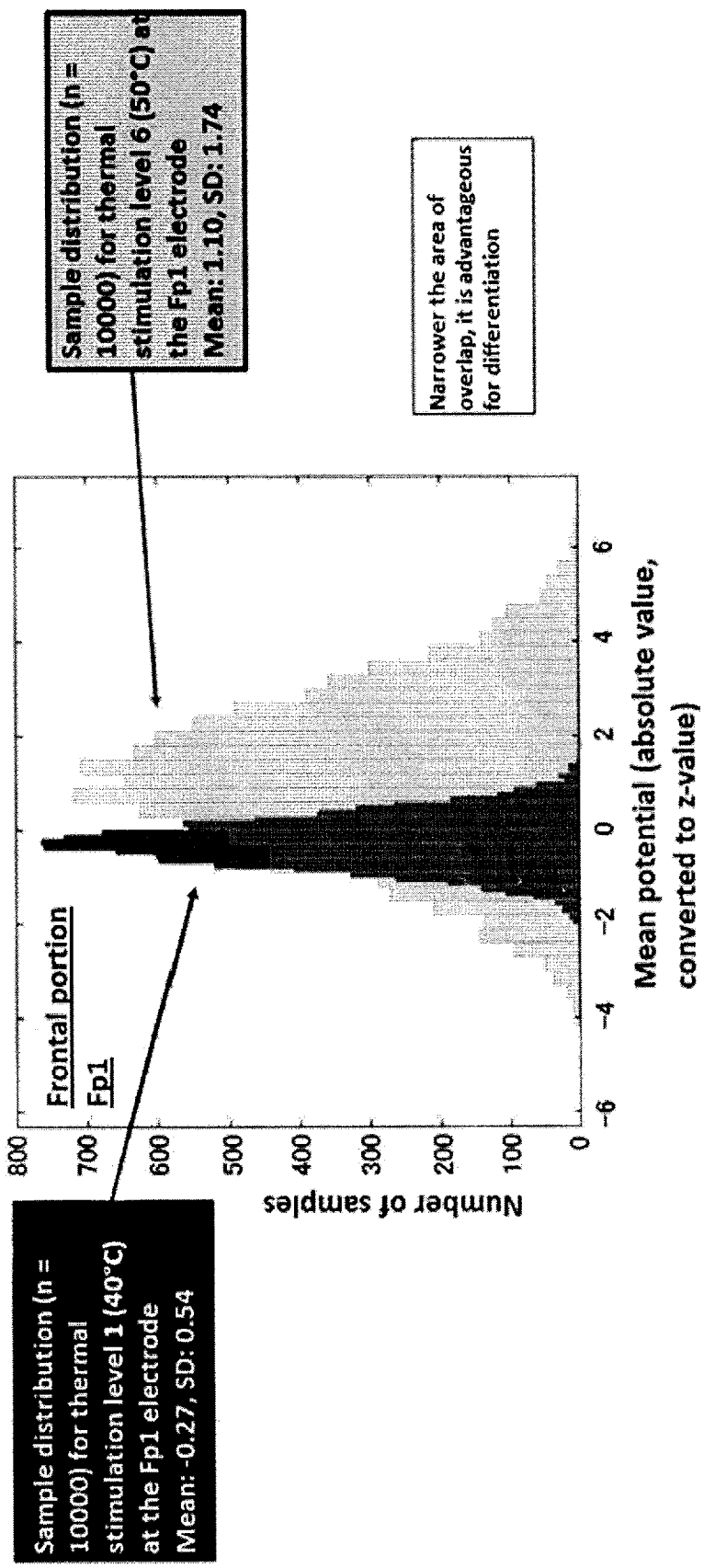
FIG. 23 shows an example of a sample distribution of a self-replicated feature (distribution 1; normal random number amplification). Normal random numbers (n=10000) with a distribution property of actually measured samples of levels 1 and 6 were generated to create a "self-replicated feature". In the graph, the sample distribution (n=10003) for thermal stimulation level 1 (40° C.) at the Fp1 electrode has a mean: −0.27 and SD: 0.54, and the y axis indicates the number of samples, and the x axis indicates the mean potential (absolute value, converted to z-value). The sample distribution (n=10000) for thermal stimulation level 6 (50° C.) at the Fp1 electrode has a mean: 1.10 and SD: 1.74. A narrower area of overlap is advantageous for differentiation.
Figure 24:
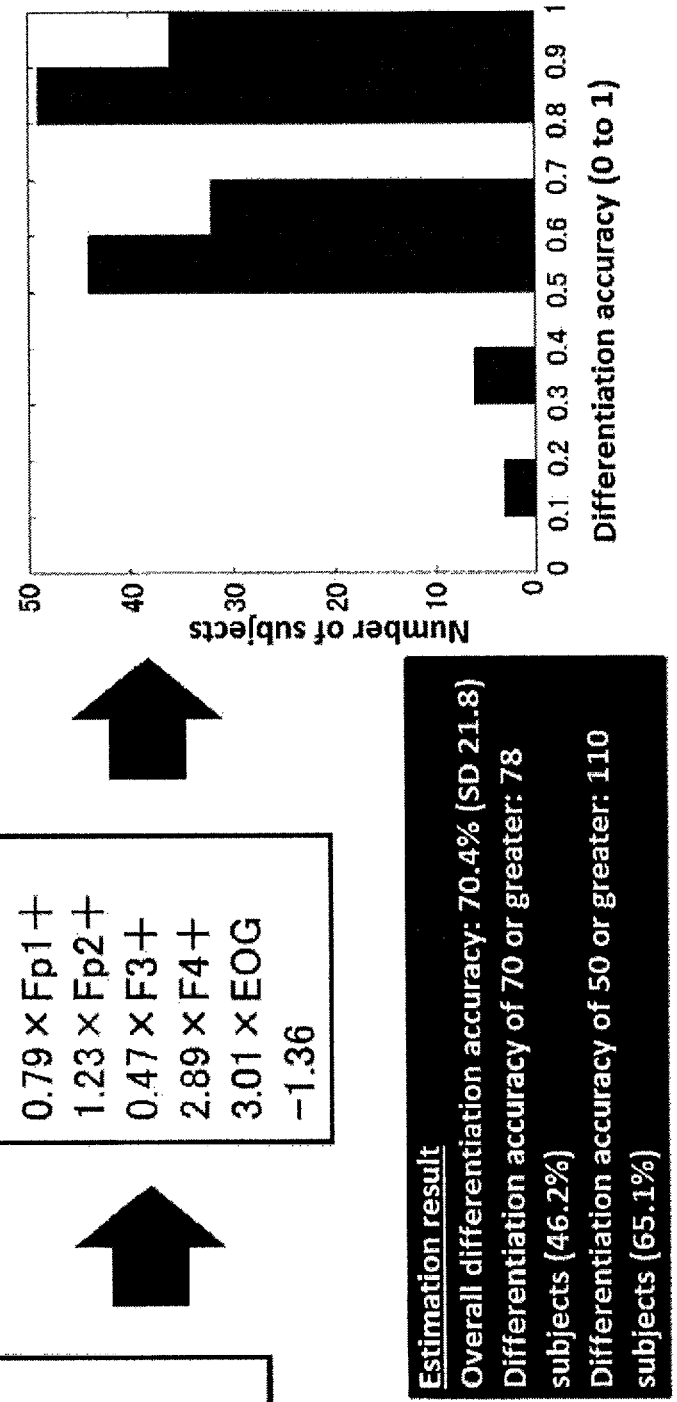
FIG. 24 shows a generalization example of an individual differentiation model (generalization 1; normal random number amplification). A feature coefficient for an individual (ID 185) differentiation model was obtained, a differentiation model was determined, and level 1 and level 6 pain differentiation and estimation was performed for different subjects (n=169). The estimation results was as follows: overall differentiation accuracy: 70.4% (SD 21.8), differentiation accuracy of 70 or greater: 78 subjects (46.2%), and differentiation accuracy of 50 or greater: 110 subjects (65.1%).

In this regard, FIG. 23 is a result of first using normal random numbers to self-replicate distribution properties of both levels and amplifying samples at each electrode to 10000. With this amplification method, replicated samples with a property of normal distribution were obtained, enabling the creation of a differentiation model at individual levels. FIG. 24 shows an individual differentiation model obtained by determining a hyperparameter with Bayesian optimization using a logistic regression model. The weighting coefficients of five electrode features were "Fp1=0.79", "Fp2=1.23", "F3=0.47", "F4=2.89", and "EOG=3.01", and the model intercept was "−1.36". When this logistic regression model was used and the degree of unpleasantness of pain of the remaining 169 subjects were differentiated and estimated using samples of levels 1 and 6 (2 levels×3 samples), the mean differentiation accuracy reached "70%". Subjects with a correct answer rate of 70% or greater reached about half the number of subjects, and subjects with that greater than the chance level reached about 70%.

Figure 25:
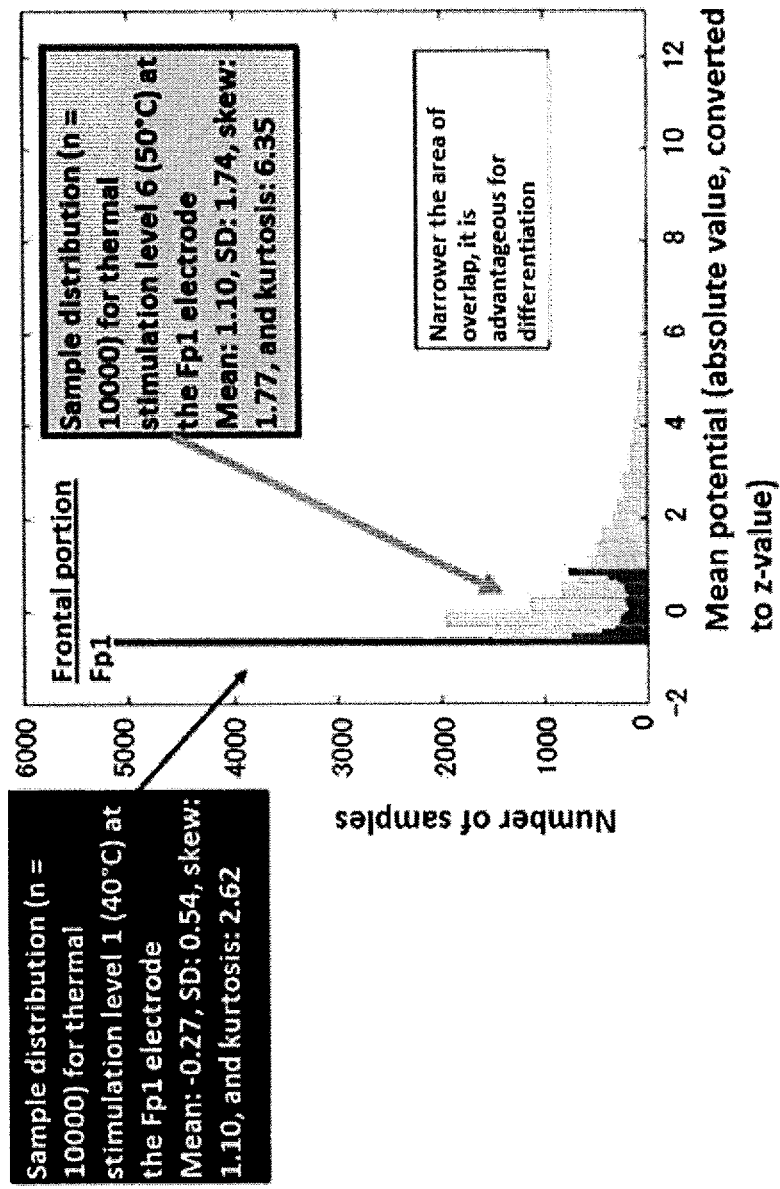
FIG. 25 shows an example of a sample distribution of a self-replicated feature (sample distribution 2; Pearson system random number amplification). The vertical axis is the number of samples, and the horizontal axis is the mean potential (absolute value, converted to a z-value). Pearson system random numbers (n=10000) with a distribution property of actually measured 30000 samples of level 1 and level 6 were generated to create a "self-replicated feature". The sample distribution (n=10000) for thermal stimulation level 1 (40° C.) at the Fp1 electrode had a mean: −0.27, SD: 0.54, skew: 1.10, and kurtosis: 2.62. The sample distribution (n=10000) for thermal stimulation level 6 (50° C.) at the Fp1 electrode had a mean: 1.10, SD: 1.74, skew: 1.77, and kurtosis: 6.35. A narrower area of overlap is advantageous for differentiation.
Figure 26:
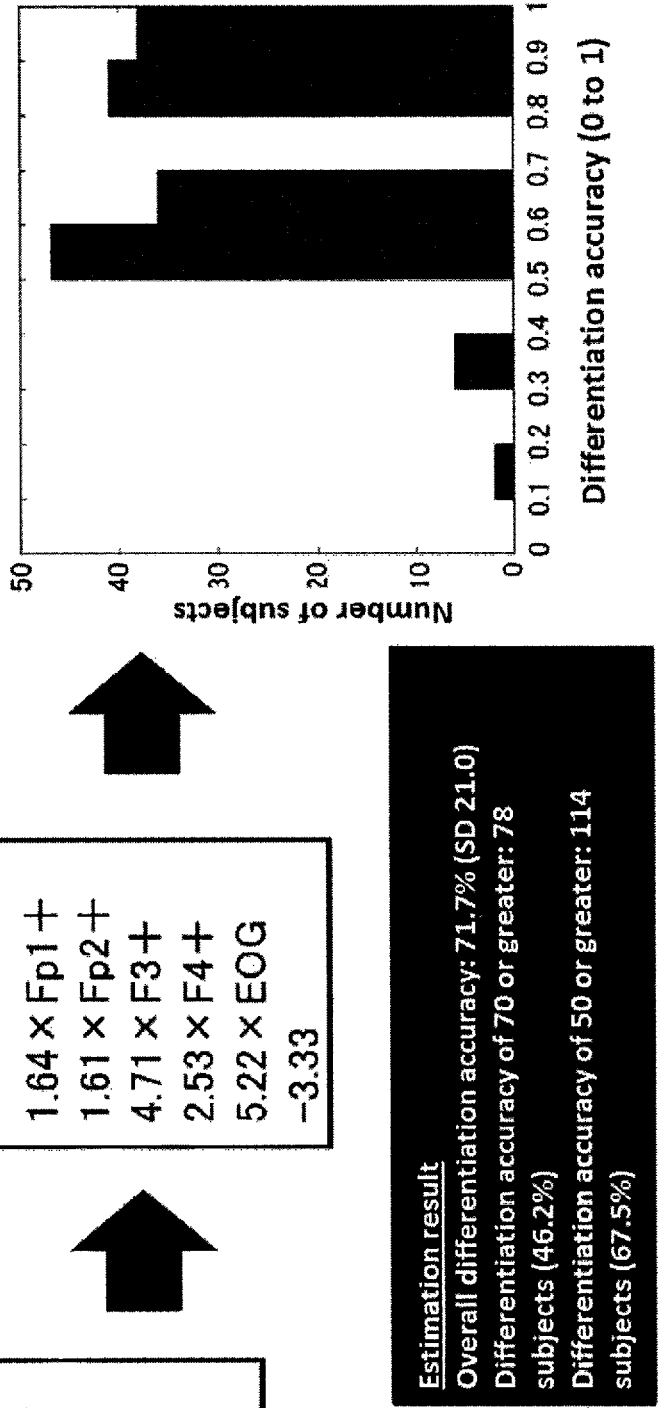
FIG. 26 shows a generalization example of an individual differentiation model (generalization 2; Pearson system random number amplification). A feature coefficient for individual (ID 185) differentiation model was obtained, a differentiation model was determined, and level 1 and level 6 pain differentiation and estimation was performed for a different subject (n=169). The estimation results was as follows; overall differentiation accuracy: 71.7% (SD 21.0), differentiation accuracy of 70 or greater: 78 subjects (46.2%), and differentiation accuracy of 50% or greater: 114 subjects (67.5%).

Next, the same 30003 samples at each level were used for sample amplification using the Pearson system random number generation method. This is a method of amplifying samples using kurtosis and skew information in addition to mean and SD. FIG. 25 shows the distribution properties of samples (10000 each) amplified at each level. In the distributions of both levels, level 6 has a longer tail, and non-overlapping areas can be clearly seen. FIG. 26 shows a differentiation model created from such replicated samples. The coefficients of five features were "Fp1=1.84", "Fp2=1.61", "F3=4.71", "F4=2.53", and "EOG=5.22", and the model intercept was "−3.33". The mean differentiation accuracy for 169 subjects using this model was "72%", which was about 2% higher compared to a model using normal random numbers. Subjects with a correct answer rate of 70% or greater reached about 50%, and subjects with that greater than the chance level increased by about 4 subjects, reaching 114 subjects and about 70%.

Figure 27:
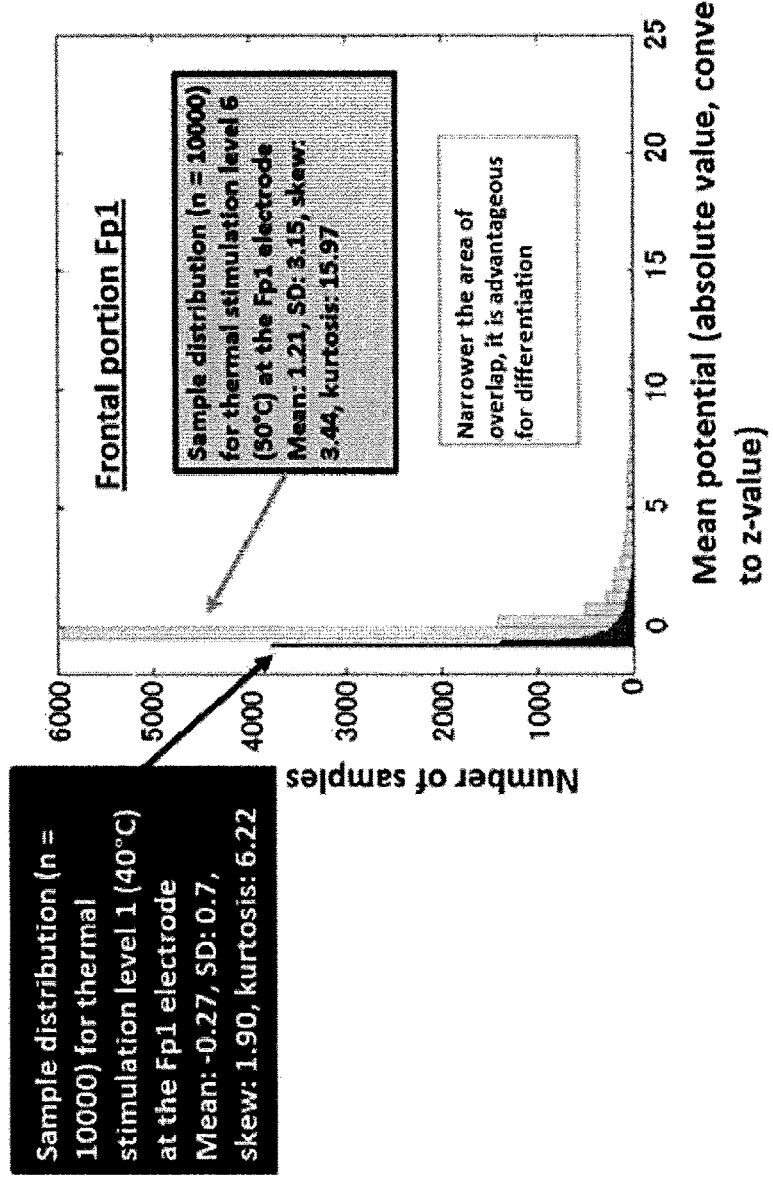
FIG. 27 shows an example of a sample distribution of a self-replicated feature (sample distribution 3; Pearson system random number amplification). Pearson system random numbers (n=10000) were generated from a distribution property of few observed samples (10 samples for each level) to create a "self-replicated feature". The sample distribution (n=10000) for thermal stimulation level 1 (40°

Lastly, a method of literally amplifying a few samples to a large number of samples was tested using a Pearson system random number generation method with a comparatively higher differentiation accuracy. In this regard, 5 to 15 seconds after application of stimulation was divided into 10, and the absolute mean amplitude for each second was calculated. The number of samples at each level and each electrode was only 30. The distribution properties (mean, SD, kurtosis, and skew) of each 30 samples were calculated, and 10000 samples were replicated and amplified at each level and electrode. The results thereof are shown in FIG. 27. Compared to the large samples of FIG. 25, distribution properties with a rather natural and smooth curve are exhibited. When a logistic regression model was created using this sample, the model in FIG. 28 was obtained ("Fp1=0.85", "Fp2=0.62", "F3=1.54", "F4=1.09", and "EOG=0.81", and the model intercept was "−0.93"). The differentiation accuracy for 169 subjects slightly increased and reached "72%". The increase of 6 subjects with a correct answer rate of 70% can be considered as contributing to the improvement in accuracy.

This Example is an experiment tackling the problem of how samples can be collected efficiently from an object in a short period of time to create an unpleasant pain differentiation model customized for an individual under a pain monitoring situation where various restrictions are expected. This experiment uses only three pain stimulations at each level as well as a condition of short application of 15 seconds. Even if there is a need to create an improvised pain differentiation model on the spot in a clinical setting and reference stimulation with no pain and with pain is applied to a clinical group under the same condition as this Example, this would require only about 2 minutes of time. It is noteworthy that a differentiation model customized for an individual can be created if the sample amplification method in this Example is used to create a self-replicated feature, even with such limited samples. This can be one of the important elemental technologies in pain differentiation apparatuses. This can be also be considered as a technology that is highly extendable in that the sample amplification in this Example is also used effectively in relatively few event-related potential features extracted in Examples 2 and 3.

(Note)

As disclosed above, the present invention has been exemplified by the use of its preferred embodiments. However, it is understood that the scope of the present invention should be interpreted based solely on the Claims. It is also understood that any patent, patent application, and references cited herein should be incorporated herein by reference in the same manner as the contents are specifically described herein. The present application claims priority to Japanese Patent Application No. 2017-146553 (filed on Jul. 28, 2017). The entire content thereof is incorporated herein by reference.

INDUSTRIAL APPLICABILITY

The present invention can determine pleasantness/unpleasantness, and administer diagnosis and therapy associated with pleasantness/unpleasantness in more detail.

REFERENCE SIGNS LIST

1000: stimulation application unit
1500: object
2000: brainwave data obtaining unit
2500: electroencephalograph
3000: pleasantness/unpleasantness determination value generation unit
4000: pleasantness/unpleasantness determination unit
5099: object
5100: pleasantness/unpleasantness determination system
5200: brainwave measurement unit
5220: electroencephalograph
5250: brainwave recording sensor
5270: brainwave amplification unit
5300: pleasantness/unpleasantness determination apparatus
5400: brainwave signal processing unit
5500: brainwave feature extraction unit
5600: pleasantness/unpleasantness determination unit
5700: pleasantness/unpleasantness determination value generation unit
5800: determination level visualization unit
5900: stimulation apparatus unit
5920: stimulation application unit
5960: stimulation information visualization unit

The invention claimed is:

1. A method of determining whether a pain corresponds to stress or unpleasantness, comprising:
   a) providing the computer implementing an unpleasantness determination classifier for determining whether a pain corresponds to stress or unpleasantness of an object, wherein the computer includes a processor and the unpleasantness determination classifier is generated by a machine learning process; and
   b) obtaining, by the processor, brainwave data or analysis data thereof from the object and applying the data to the unpleasantness determination classifier to determine unpleasantness of the object, wherein the machine learning process includes,
   c) applying the different stimuli to the object under the same environment to obtain each brainwave data or analysis data thereof by using the brainwave recording sensor, wherein the brainwave recording sensor has a plurality of electrodes including brainwave measurement electrodes configured to be placed on a subject's scalp,
   d) associating, by the processor, a difference in the brainwave data or analysis data thereof obtained under the same environment with a reaction of the object to the stimulation, and
   e) generating, by the processor, the unpleasantness determination classifier based on the association, wherein the generating the unpleasantness determination classifier includes,
      i) preprocessing the brainwave data by filtering to remove noises of eye blinking and myogenic potential and by normalizing the filtered brainwave data based on the brainwave data during a first predetermined period before applying the stimulation, and
      ii) generating the unpleasantness determination classifier by machine learning with feature selection based on first and second brainwave data, wherein the first brainwave data are the preprocessed brainwave data during a second predetermined period after applying a first level of the stimulation corresponding to unpleasantness, and the second brainwave data are the preprocessed brainwave data during the second predetermined period after applying a second level of the stimulation corresponding to pleasantness, wherein the associating the difference includes,
   extracting features by converting the brainwave data into the mean value of amplitude and the frequency power during the second predetermined period; and generating, using Support Vector Machine Recursive Feature Elimination method, the unpleasantness determination classifier by ranking the features and eliminating the feature with the lowest contribution.

2. The method of claim 1, wherein the brainwave data or analysis data thereof comprises at least one brainwave feature selected from:

Electrode position: positions on the scalp from a frontal portion to a parietal portion, and over an occipital position; positions in accordance with the international 10-20 system, or positions at a specific uniform distance; and Time frame: 0 to 100, 100 to 200, 200 to 300, 300 to 400, 400 to 500, 500 to 600, 600 to 700, or 700 to 800 milliseconds, or a combination of smaller time segments or longer time frames and/or wherein the brainwave feature comprises at least one selected from the group consisting of Fp1, Fp2, Fpz, F3, F4, Fz, C3, C4, Cz, P3, P4, and Pz.

3. The method of claim 1, wherein the unpleasantness determination classifier materializes determination of unpleasantness with a negative potential level for a waveform during latency compared to a standard waveform.

4. The method of claim 3, wherein the negative potential level is based on a waveform in a range after 150 milliseconds from stimulation or a range after 300 milliseconds from stimulation or a range of 300 milliseconds to 800 milliseconds after stimulation or a range of 300 milliseconds to 800 milliseconds after stimulation.

5. The method of claim 3, wherein the negative potential level is based on a negative occupancy in a range of 300 milliseconds to 800 milliseconds after stimulation.

6. A method of determining whether a pain corresponds to stress or unpleasantness, comprising:

a) providing the computer implementing an unpleasantness determination classifier for determining whether a pain corresponds to stress or unpleasantness of an object, wherein the computer includes a processor and the unpleasantness determination classifier is generated by a machine learning process; and b) obtaining, by the processor, brainwave data or analysis data thereof from the object and applying the data to the unpleasantness determination classifier to determine unpleasantness of the object, wherein the machine learning process includes, c) applying the different stimuli to the object under the same environment to obtain each brainwave data or analysis data thereof by using the brainwave recording sensor, wherein the brainwave recording sensor has a plurality of electrodes including brainwave measurement electrodes configured to be placed on a subject's scalp, d) associating, by the processor, a difference in the brainwave data or analysis data thereof obtained under the same environment with a reaction of the object to the stimulation, and e) generating, by the processor, the unpleasantness determination classifier based on the association, wherein the generating the unpleasantness determination classifier includes, i) preprocessing the brainwave data by filtering to remove noises of eye blinking and myogenic potential and by normalizing the filtered brainwave data based on the brainwave data during a first predetermined period before applying the stimulation, and ii) generating the unpleasantness determination classifier by machine learning with feature selection based on first and second brainwave data, wherein the first brainwave data are the preprocessed brainwave data during a second predetermined period after applying a first level of the stimulation corresponding to unpleasantness, and the second brainwave data are the preprocessed brainwave data during the second predetermined period after applying a second level of the stimulation corresponding to pleasantness, wherein the associating the difference includes, extracting features by converting the brainwave data into the absolute value of amplitude during the second predetermined period and converting thereinto z values; and generating the unpleasantness determination classifier by using LASSO and Bayesian optimization method.

7. The method of claim 6, further comprising self-replicating the brainwave data for a model or analysis data thereof to increase the number of the brainwave data or analysis data thereof.

8. The method of claim 7, wherein the self-replication is performed based on a distribution property and/or wherein the self-replication is performed by generating a normal random number or a Pearson system random number.

9. A system for determining stress or unpleasantness of an object, comprising:

a brainwave recording sensor, wherein the brainwave recording sensor has a plurality of electrodes including brainwave measurement electrodes configured to be placed on a subject's scalp, a first computer including a first processor, the first processor configured to i) obtain, by using the brainwave recording sensor, brainwave data or analysis data thereof from the object and ii) perform, based on the obtained brainwave data or analysis data thereof, a process as an unpleasantness determination classifier for determining whether a pain corresponds to stress or unpleasantness of the object, the classifier generated by a machine learning process; and a second computer including a second processor, the second processor configured to execute the machine learning process, the machine learning process including, a) applying the different stimuli to the object under the same environment to obtain each brainwave data or analysis data thereof by using the brainwave recording sensor, b) associating, by the second processor, a difference in the brainwave data or analysis data thereof obtained under the same environment with a reaction of the object to the stimulation, and c) generating, by the second processor, the unpleasantness determination classifier based on the association, wherein the generating the unpleasantness determination classifier includes, i) preprocessing the brainwave data by filtering to remove noises of eye blinking and myogenic potential and by normalizing the filtered brainwave data based on the brainwave data during a first predetermined period before applying the stimulation, and ii) generating the unpleasantness determination classifier by machine learning with feature selection based on first and second brainwave data, wherein the first brainwave data are the preprocessed brainwave data during a second predetermined period after applying a first level of the stimulation corresponding to unpleasantness, and the second brainwave data are the preprocessed brainwave data during the second predetermined period after applying a second level of the stimulation corresponding to pleasantness, wherein the associating the difference includes, extracting features by converting the brainwave data into the mean value of amplitude and the frequency power during the second predetermined period; and generating, using Support Vector Machine Recursive Feature Elimination method, the unpleasantness determination classifier by ranking the features and eliminating the feature with the lowest contribution.

10. A system for determining stress or unpleasantness of an object, comprising:
- a brainwave recording sensor, wherein the brainwave recording sensor has a plurality of electrodes including brainwave measurement electrodes configured to be placed on a subject's scalp,
- a first computer including a first processor, the first processor configured to
  - i) obtain, by using the brainwave recording sensor, brainwave data or analysis data thereof from the object and
  - ii) perform, based on the obtained brainwave data or analysis data thereof, a process as an unpleasantness determination classifier for determining whether a pain corresponds to stress or unpleasantness of the object, the classifier generated by a machine learning process; and
- a second computer including a second processor, the second processor configured to execute the machine learning process, the machine learning process including,
  - a) applying the different stimuli to the object under the same environment to obtain each brainwave data or analysis data thereof by using the brainwave recording sensor,
  - b) associating, by the second processor, a difference in the brainwave data or analysis data thereof obtained under the same environment with a reaction of the object to the stimulation, and
  - c) generating, by the second processor, the unpleasantness determination classifier based on the association, wherein the generating the unpleasantness determination classifier includes,
    - i) preprocessing the brainwave data by filtering to remove noises of eye blinking and myogenic potential and by normalizing the filtered brainwave data based on the brainwave data during a first predetermined period before applying the stimulation, and
    - ii) generating the unpleasantness determination classifier by machine learning with feature selection based on first and second brainwave data, wherein the first brainwave data are the preprocessed brainwave data during a second predetermined period after applying a first level of the stimulation corresponding to unpleasantness, and the second brainwave data are the preprocessed brainwave data during the second predetermined period after applying a second level of the stimulation corresponding to pleasantness, wherein the associating the difference includes, extracting features by converting the brainwave data into the absolute value of amplitude during the second predetermined period and converting thereinto z values; and generating the unpleasantness determination classifier by using LASSO and Bayesian optimization method.

* * * * *